(12) United States Patent
Lesuisse et al.

(10) Patent No.: US 7,166,629 B2
(45) Date of Patent: *Jan. 23, 2007

(54) AMINOINDAZOLE DERIVATIVES AS MEDICAMENTS AND PHARMACEUTICAL COMPOSITIONS INCLUDING THEM

(75) Inventors: Dominique Lesuisse, Montreuil (FR); Gilles Dutruc-Rosset, Paris (FR); Franck Halley, Sevres (FR); Didier Babin, Montigny (FR); Thomas Rooney, Orsay (FR)

(73) Assignee: Aventis Pharma S.A., Paris (FR)

( * ) Notice: Subject to any disclaimer, the term of this patent is extended or adjusted under 35 U.S.C. 154(b) by 232 days.

This patent is subject to a terminal disclaimer.

(21) Appl. No.: 10/654,703

(22) Filed: Sep. 4, 2003

(65) Prior Publication Data

US 2004/0110956 A1 Jun. 10, 2004

(30) Foreign Application Priority Data

Sep. 5, 2002 (FR) .................................. 02 10962

(51) Int. Cl.
*A61K 31/416* (2006.01)
*C07D 231/56* (2006.01)

(52) U.S. Cl. .................. 514/397; 514/405; 548/311.7; 548/362.1

(58) Field of Classification Search ............. 548/362.1, 548/311.7; 514/397, 405
See application file for complete search history.

(56) References Cited

U.S. PATENT DOCUMENTS

| 4,751,302 | A  | * | 6/1988 | Ibuki et al. ............ 544/140 |
| 6,613,776 | B2 | * | 9/2003 | Knegtel et al. ......... 514/300 |
| 6,949,579 | B2 | * | 9/2005 | Dutruc-Rosset et al. .. 514/403 |

FOREIGN PATENT DOCUMENTS

| WO | WO 02/22603 | 3/2002 |
| WO | WO 02/50065 | 6/2002 |
| WO | WO 02/50066 | 6/2002 |

\* cited by examiner

*Primary Examiner*—Laura L. Stockton
(74) *Attorney, Agent, or Firm*—Irving Newman

(57) ABSTRACT

The present invention relates to novel derivatives of general formula (I)

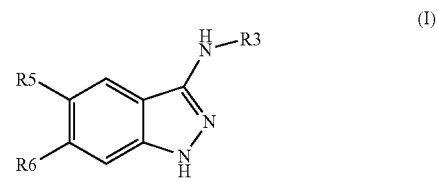

in which
R3 is a (1–6C)alkyl, aryl, aryl(1–6C)alkyl, heteroaryl, heteroaryl(1–6C)alkyl, aryl or heteroaryl fused to a (1–10C)cycloalkyl, heterocycle, heterocycloalkyl, cycloalkyl, adamantyl, polycycloalkyl, alkenyl, alkynyl, CONR1R2, COOR1, SO$_2$R1, C(=NH)R1 or C(=NH)NR1 radical;

R5 and R6 are, independently of one another, chosen from the following radicals: halogen, CN, NO$_2$, NH$_2$, OH, COOH, C(O)OR8, —O—C(O)R8, NR8R9, NHC(O) R8, C(O)NR8R9, NHC(S)R8, C(S)NR8R9, SR8, S(O) R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl or polycycloalkyl.

6 Claims, No Drawings

AMINOINDAZOLE DERIVATIVES AS MEDICAMENTS AND PHARMACEUTICAL COMPOSITIONS INCLUDING THEM

The present invention relates to the use of derivatives of formula (I):

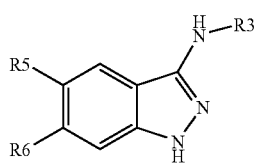

or their pharmaceutically acceptable salts as kinase inhibitor.

The subject matter of the invention is the use of the aminoindazole derivatives of formula (I) and their pharmaceutically acceptable salts in the preparation of pharmaceutical compositions intended to prevent and treat diseases which can result from an abnormal activity of kinases, such as, for example, those involved in neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer, the pharmaceutical compositions comprising the novel aminoindazole derivatives and their pharmaceutically acceptable salts and the novel aminoindazole derivatives and their pharmaceutically acceptable salts.

The present invention relates to derivatives of formula (I) in which:
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;
R5 and R6 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O) R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;
R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;
R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S) R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

More particularly, the present invention relates to derivatives of formula (I) in which:
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C)alkyl;
R5 is an aryl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O) R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;
R6 is a halogen, methyl, cyclopropyl, CN, OH, methoxy, trifluoromethyl, ethylenyl, acetylenyl, trifluoromethoxy, NO$_2$, NH$_2$ or NMe2 radical;
R1, R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy;
R1 and R2 can form a 5- or 6-membered ring which may or may not have a heteroatom, such as O, S or N;

to their racemates, enantiomers or diastereoisomers and their mixtures, to their tautomers and to their pharmaceutically acceptable salts.

The present invention preferably relates to derivatives of formula (I) in which:
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C)alkyl;

R5 is a phenyl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R6 is a halogen, methyl, cyclopropyl, CN, OH, methoxy, trifluoromethyl, ethylenyl, acetylenyl, trifluoromethoxy, NO$_2$, NH$_2$ or NMe$_2$ radical;

R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy;

R1 and R2 can form a 5- or 6-membered ring which may or may not have a heteroatom, such as O, S or N;

to their racemates, enantiomers, diastereoisomers and their mixtures, to their tautomers and to their pharmaceutically acceptable salts.

The present invention preferably relates to derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C)cycloalkyl, heterocycle, heterocycloalkyl, cycloalkyl, adamantyl, polycycloalkyl, alkenyl, alkynyl, CONR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, trifluoromethyl, trifluoromethylsulfanyl, trifluoromethoxy or (1–6C)alkyl;

R5 is a phenyl;

R6 is a chlorine;

R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy; to their isomers, to their mixtures, to their racemates, enantiomers, diastereoisomers or tautomers, and to their pharmaceutically acceptable salts.

In the preceding definitions and those which follow, the (1–6C)alkyl radicals comprise 1 to 6 carbon atoms in a straight- or branched-chain; the alkenyl radicals comprise 2 to 6 carbon atoms and one to 3 conjugated or nonconjugated double bonds in a straight- or branched-chain; the alkynyl radicals comprise 2 to 6 carbon atoms and one to 3 conjugated or nonconjugated triple bonds in a straight- or branched-chain; the aryl radicals are chosen from phenyl, naphthyl or indenyl; the heteroaryl radicals comprise 3 to 10 ring members, optionally comprising one or more heteroatoms chosen from oxygen, sulfur and nitrogen, in particular, thiazolyl, thienyl, pyrrolyl, pyridinyl, furyl, imidazolyl, oxazolyl, pyrazinyl, tetrazolyl, oxadiazolyl, thiadiazolyl, isoxadiazolyl, isothiadiazolyl, isothiazolyl, isoxazolyl, triazolyl, pyrazolyl or indolyl; the halogen radical is either chlorine, iodine, fluorine or bromine; the polycycloalkyl radicals are chosen from adamantyl, quinuclidinyl, bornanyl, norbornanyl, bornenyl or norbornenyl; the heteroaryl radicals fused to a (1–10C)cycloalkyl are chosen from indanyl, isochromanyl, chromanyl, 1,2,3,4-tetrahydroisoquinolyl or 1,2,3,4-tetrahydroquinolyl; the heterocycle radicals comprise 1 to 2 heteroatoms chosen from oxygen, sulfur or nitrogen and represent in particular piperidinyl, morpholinyl, pyrrolidinyl, imidazolidinyl, pyrazolidinyl, isothiazolidinyl, thiazolidinyl, isoxazolidinyl, oxazolidinyl, piperazinyl, azetidinyl, 2-piperidone, 3-piperidone, 4-piperidone, 2-pyrrolidone or 3-pyrrolidone.

The compounds of formula (I) exhibiting one or more asymmetric carbons and can therefore exist in the form of isomers, of racemates, of enantiomers and of diastereoisomers; the latter also form part of the invention, as do their mixtures.

Mention may be made, among the compounds of formula (I) of use according to the invention, of the following compounds:

N-(bicyclo[2.2.1]hept-5-en-2-ylmethyl)-6-chloro-5-phenyl-1H-indazol-3-amine 6-chloro-N-(3,3-dimethylbutyl)-5-phenyl-1H-indazol-3-amine 6-chloro-N-(3-phenylpropyl)-5-phenyl-1H-indazol-3-amine 6-chloro-N-(cyclopropylmethyl)-5-phenyl-1H-indazol-3-amine 6-chloro-N-(cyclopentylmethyl)-5-phenyl-1H-indazol-3-amine 6-chloro-N-[3-(methylthio)propyl]-5-phenyl-1H-indazol-3-amine 6-chloro-N-(phenylethyl)-5-phenyl-1H-indazol-3-amine 6-chloro-N-(cyclohexylmethyl)-5-phenyl-1H-indazol-3-amine 6-chloro-N-propyl-5-phenyl-1H-indazol-3-amine 6-chloro-N-(2,2,3,3,4,4,4-heptafluorobutyl)-5-phenyl-1H-indazol-3-amine hydrate 6-chloro-N-(4,4,4-trifluorobutyl)-5-phenyl-1H-indazol-3-amine 6-chloro-N-[(4-methoxyphenyl)methyl]-5-phenyl-1H-indazol-3-amine 6-chloro-N-(phenylmethyl)-5-phenyl-1H-indazol-3-amine 6-chloro-N-[(4-cyanophenyl)methyl]-5-phenyl-1H-indazol-3-amine N-[(4-chlorophenyl)methyl]-6-chloro-5-phenyl-1H-indazol-3-amine 6-chloro-N-[(3-methoxyphenyl)methyl]-5-phenyl-1H-indazol-3-amine 6-chloro-N-[[4-(trifluoromethoxy)phenyl]methyl]-5-phenyl-1H-indazol-3-amine N-[4-[[[6-chloro-5-phenyl-1H-indazol-3-yl]amino]methyl]phenyl]acetamide 6-chloro-N-[(3,5-dichlorophenyl)methyl]-5-phenyl-1H-indazol-3-amine 6-chloro-5-phenyl-N-[[4-(trifluoromethyl)phenyl]methyl]-1H-indazol-3-amine 6-chloro-N-[(4-fluorophenyl)methyl]-5-phenyl-1H-indazol-3-amine 6-chloro-N-[3-(4-methylphenoxy)phenylmethyl]-5-phenyl-1H-indazol-3-amine N-(2,2,3,3,4,4,4-heptafluorobutyl)-6-chloro-5-phenyl-1H-indazol-3-amine 6-chloro-5-phenyl-N-[[3,5-bis(trifluoromethyl)phenyl]methyl]-1H-indazol-3-amine 6-chloro-5-phenyl-N-[[3-(trifluoromethyl)phenyl]methyl]-1H-indazol-3-amine 6-chloro-N-[(6-methoxy-2-naphthyl)methyl]-5-phenyl-1H-indazol-3-amine
6-chloro-N-[(pentafluorophenyl)methyl]-5-phenyl-1H-indazol-3-amine
6-chloro-N-[[4-(methylthio)phenyl]methyl]-5-phenyl-1H-indazol-3-amine
N-[(4-chloro-3-fluorophenyl)methyl]-6-chloro-5-phenyl-1H-indazol-3-amine
6-chloro-5-phenyl-N-(3,3,3-trifluoropropyl)-1H-indazol-3-amine
6-chloro-5-phenyl-N-(3-thienylmethyl)-1H-indazol-3-amine
N-(bicyclo[2.2.1]hept-5-en-2-ylmethyl)-6-chloro-5-phenyl-1H-indazol-3-amine
N-(1,1'-biphenyl-4-ylmethyl)-6-chloro-5-phenyl-1H-indazol-3-amine
6-chloro-N-[[4-(dimethylamino)phenyl]methyl]-5-phenyl-1H-indazol-3-amine
N-(2,2'-bithiophen-5-ylmethyl)-6-chloro-5-phenyl-1H-indazol-3-amine
6-chloro-5-phenyl-N-[[1-(phenylmethyl)-1H-imidazol-2-yl]methyl]-1H-indazol-3-amine
6-chloro-N-[[1-methyl-1H-imidazol-2-yl]methyl]-5-phenyl-1H-indazol-3-amine
6-chloro-N-[(1-methyl-1H-indol-3-yl)methyl]-5-phenyl-1H-indazol-3-amine
6-chloro-N-[(5-methyl-2-furanyl)methyl]-5-phenyl-1H-indazol-3-amine
6-chloro-5-phenyl-N-(1H-pyrrol-2-ylmethyl)-1H-indazol-3-amine
6-chloro-5-phenyl-N-[(1H-imidazol-2-yl)methyl]-1H-indazol-3-amine
6-chloro-5-phenyl-N-[(1H-imidazol-4-yl)methyl]-1H-indazol-3-amine
6-chloro-5-phenyl-N-(1H-pyrazol-3-ylmethyl)-1H-indazol-3-amine
6-chloro-N-[[2-methyl-1H-imidazol-4-yl]methyl]-5-phenyl-1H-indazol-3-amine
6-chloro-N-[(3,5-dimethyl-1-phenyl-1H-pyrazol-4-yl)methyl]-5-phenyl-1H-indazol-3-amine
6-chloro-5-phenyl-N-[[2-phenyl-1H-imidazol-4-yl]methyl]-1H-indazol-3-amine
6-chloro-N-[[5-(4-chlorophenyl)-2-furanyl]methyl]-5-phenyl-1H-indazol-3-amine
6-chloro-5-phenyl-N-[(1-methyl-1H-pyrrol-2-yl)methyl]-1H-indazol-3-amine
4-[5-[[[6-chloro-5-phenyl-1H-indazol-3-yl]amino]methyl]-2-furanyl]-benzenesulfonamide
6-chloro-5-phenyl-N-(3-thienylmethyl)-1H-indazol-3-amine
6-chloro-5-phenyl-N-[[2-phenyl-1H-imidazol-4-yl]methyl]-1H-indazol-3-amine
ethyl 2-[[[6-chloro-5-phenyl-1H-indazol-3-yl]amino]methyl]-5-(methylthio)-1H-imidazole-4-carboxylate
6-chloro-5-phenyl-N-[[5-[4-(trifluoromethyl)phenyl]-2-furanyl]methyl]-1H-indazol-3-amine
6-chloro-5-phenyl-N-[2-(1-piperidinyl)ethyl]-1H-indazol-3-amine
6-chloro-N-[2-(4-morpholinyl)ethyl]-5-phenyl-1H-indazol-3-amine
N-(6-chloro-5-phenyl-1H-indazol-3-yl)-N'-(3,5-dichlorophenyl)urea
N-(6-chloro-5-phenyl-1H-indazol-3-yl)-N'-(2-propenyl)urea
N-(6-chloro-5-phenyl-1H-indazol-3-yl)-N'-(phenylmethyl)urea
N-(6-chloro-5-phenyl-1H-indazol-3-yl)-N'-(4-phenoxyphenyl)urea
N-(6-chloro-5-phenyl-1H-indazol-3-yl)-N'-(4-methoxyphenyl)methyl]urea
N-(6-chloro-5-phenyl-1H-indazol-3-yl)-N'-[4-(trifluoromethyl)phenyl]urea
N-(6-chloro-5-phenyl-1H-indazol-3-yl)-N'-(4-methoxyphenyl)urea
N-(6-chloro-5-phenyl-1H-indazol-3-yl)-N'-cyclohexylurea
N-(6-chloro-5-phenyl-1H-indazol-3-yl)-N'-propyl urea
N-(6-chloro-5-phenyl-1H-indazol-3-yl)-N'-(4-chlorophenyl)urea
N-(6-chloro-5-phenyl-1H-indazol-3-yl)-N'-(4-fluorophenyl)urea
N-[6-chloro-5-phenyl-1H-indazol-3-yl]-N'-(tricyclo[3.3.1.1$^{3,7}$]dec)-1-ylurea
N-(6-chloro-5-phenyl-1H-indazol-3-yl)-N'-(4-methylphenyl)urea
N-[6-chloro-5-phenyl-1H-indazol-3-yl]4-methyl-benzenesulfonamide
N-[6-chloro-5-phenyl-1H-indazol-3-yl]methanesulfonamide
N-[6-chloro-5-phenyl-1H-indazol-3-yl]-2-propanesulfonamide
N-[6-chloro-5-phenyl-1H-indazol-3-yl]-2,2,2-trifluoroethanesulfonamide
N-[6-chloro-5-phenyl-1H-indazol-3-yl]-2-thiophenesulfonamide
N-[6-chloro-5-phenyl-1H-indazol-3-yl]benzenesulfonamide
N-[6-chloro-5-phenyl-1H-indazol-3-yl]-4-(trifluoromethyl)benzenesulfonamide
N-[6-chloro-5-phenyl-1H-indazol-3-yl]-5-(3-isoxazolyl)-2-thiophenesulfonamide
N-[6-chloro-5-phenyl-1H-indazol-3-yl]-4-fluorobenzenesulfonamide
N-[6-chloro-5-phenyl-1H-indazol-3-yl]-4-methoxybenzenesulfonamide
N-[6-chloro-5-phenyl-1H-indazol-3-yl]benzenemethanesulfonamide
N-[6-chloro-5-phenyl-1H-indazol-3-yl]-1-methyl-1H-imidazole-4-sulfonamide
N-[6-chloro-5-phenyl-1H-indazol-3-yl]-4-(1,1-dimethylethyl)benzenesulfonamide
N-[4-[[[(6-chloro-5-phenyl-1H-indazol-3-yl)amino]sulfonyl]phenyl]acetamide
N-[6-chloro-5-phenyl-1H-indazol-3-yl]-4-methylbenzenemethanesulfonamide
6-chloro-N-(pentafluorophenyl)-5-phenyl-1H-indazol-3-amine
6-chloro-N-(3,4-difluorophenyl)-5-phenyl-1H-indazol-3-amine
6-chloro-5-phenyl-N-(2,3,5,6-tetrafluorophenyl)-1H-indazol-3-amine
6-chloro-5-phenyl-N-(2,4,6-trifluorophenyl)-1H-indazol-3-amine
6-chloro-N-(4-fluorophenyl)-5-phenyl-1H-indazol-3-amine
6-chloro-N-[3-(trifluoromethyl)phenyl]-5-phenyl-1H-indazol-3-amine
6-chloro-N-[4-(trifluoromethyl)phenyl]-5-phenyl-1H-indazol-3-amine
6-chloro-N-[3-fluoro-5-(trifluoromethyl)phenyl]-5-phenyl-1H-indazol-3-amine
6-chloro-N-(4-nitrophenyl)-5-phenyl-1H-indazol-3-amine
6-chloro-N-(3-nitrophenyl)-5-phenyl-1H-indazol-3-amine
6-chloro-N-(3-methoxyphenyl)-5-phenyl-1H-indazol-3-amine 6-chloro-N-(4-methoxyphenyl)-5-phenyl-1H-indazol-3-amine
6-chloro-N,5-diphenyl-1H-indazol-3-amine
6-chloro-N-(1-pyridinyl)-5-phenyl-1H-indazol-3-amine
6-chloro-N-(2-pyridinyl)-5-phenyl-1H-indazol-3-amine their isomers, their mixtures, their racemates, enantiomers, diastereoisomers or tautomers, and their pharmaceutically acceptable salts, and more particularly the following compounds:
N-butyl-6-chloro-5-phenyl-1H-indazol-3-amine
3-(6-Chloro-5-phenyl-1H-indazol-3-ylamino)thiophene-2-carbonitrile
(6-Chloro-5-phenyl-1H-indazol-3-yl)(pyridin-2-yl)amine
(6-Chloro-5-phenyl-1H-indazol-3-yl)(5-nitropyridin-2-yl)amine
(6-Chloro-5-phenyl-1H-indazol-3-yl)(6-methoxypyridin-2-yl)amine
N-(6-Chloro-5-phenyl-1H-indazol-3-yl)-N'-phenylurea
1-(6-Chloro-5-phenyl-1H-indazol-3-yl)-3-(4-ethoxyphenyl)urea
1-(6-Chloro-5-phenyl-1H-indazol-3-yl)-3-(3,4-dichlorophenyl)urea
3-[3-(6-Chloro-5-phenyl-1H-indazol-3-yl)ureido]propionic acid methyl ester
1-(6-Chloro-5-phenyl-1H-indazol-3-yl)-3-(4-(dimethylamino)phenyl)urea
1-(6-Chloro-5-phenyl-1H-indazol-3-yl)-3-isopropylurea
1-(6-Chloro-5-phenyl-1H-indazol-3-yl)-3-cyclohexylurea
1-(6-Chloro-5-phenyl-1H-indazol-3-yl)-3-(3-(trifluoromethyl)phenyl)urea
1-(6-Chloro-5-phenyl-1H-indazol-3-yl)-3-(2-(thiophen-2-yl)ethyl)urea
1-(1,3-Benzodioxol-5-yl)-3-(6-chloro-5-phenyl-1H-indazol-3-yl)urea
1-(6-Chloro-5-phenyl-1H-indazol-3-yl)-3-(3,5-dimethylisoxazol-4-yl)urea
1-Benzyl-3-(6-chloro-5-phenyl-1H-indazol-3-yl)urea
1-(6-Chloro-5-phenyl-1H-indazol-3-yl)-3-(phenethyl)thiourea
1-(6-Chloro-5-phenyl-1H-indazol-3-yl)-3-[3-(4-methylpiperazin-1-yl)propyl]urea
1-(6-Chloro-5-phenyl-1H-indazol-3-yl)-3-(3-(imidazol-1-yl)propyl)urea
1-(6-Chloro-5-phenyl-1H-indazol-3-yl)-3-(2-hydroxyethyl)urea
1-(6-Chloro-5-phenyl-1H-indazol-3-yl)-3-[3-(4-methylpiperazin-1-yl)propyl]urea
Pyrrolidine-1-carboxylic acid (6-chloro-5-phenyl-1H-indazol-3-yl)amide
(6-Chloro-5-phenyl-1H-indazol-3-yl)carbamic acid methyl ester
(6-Chloro-5-phenyl-1H-indazol-3-yl)urea
(6-Chloro-5-phenyl-1H-indazol-3-yl)carbamic acid benzyl ester
(6-Chloro-5-phenyl-1H-indazol-3-yl)carbamic acid allyl ester
(6-Chloro-5-phenyl-1H-indazol-3-yl)carbamic acid isobutyl ester
Piperidine-1-carboxylic acid (6-chloro-5-phenyl-1H-indazol-3-yl)amide
1-(3-(Azetidin-1-yl)propyl)-3-(6-chloro-5-phenyl-1H-indazol-3-yl)urea
1-(6-Chloro-5-phenyl-1H-indazol-3-yl)-3-(3-chloropropyl)urea
1-(6,7-Difluoro-5-phenyl-1H-indazol-3-yl)-3-(3-(imidazol-1-yl)propyl)urea
1-(3-Aminopropyl)-3-(6-chloro-5-phenyl-1H-indazol-3-yl)urea
1-(6-Chloro-5-phenyl-1H-indazol-3-yl)-3-[4-(4-(pyridin-3-yl)imidazol-1-yl)-butyl]urea
1-(6-Chloro-5-phenyl-1H-indazol-3-yl)-3-(2-(pyrrolidin-1-yl)ethyl)urea
2,5-Dimethylpyrrolidine-1-carboxylic acid (6-chloro-5-phenyl-1H-indazol-3-yl)amide
N-(6-Chloro-5-phenyl-1H-indazol-3-yl)acetamidine
N-(6-Chloro-5-phenyl-1H-indazol-3-yl)-6-methoxypyrazine-2-carboxamidine
N-(6-Chloro-5-phenyl-1H-indazol-3-yl)benzamidine
N-(6-Chloro-5-phenyl-1H-indazol-3-yl)pyridine-2-carboxamidine
N-(6-chloro-5-phenyl-1H-indazol-3-yl)-3-methoxybenzenesulfonamide their isomers, their mixtures, their racemates, enantiomers, diastereoisomers or tautomers, and their pharmaceutically acceptable salts, The invention also relates to the pharmaceutical compositions comprising, as active principle, a derivative of formula (I) in which R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5 and R6 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)

R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

The present invention relates more particularly to the pharmaceutical compositions comprising, as active principle, a derivative of formula (I) in which:

R3 is a (1–6C)alkyl, aryl, aryl(1–6C)alkyl; heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C)alkyl;

R5 is an aryl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R6 is a halogen, methyl, cyclopropyl, CN, OH, methoxy, trifluoromethyl, ethylenyl, acetylenyl, trifluoromethoxy, NO$_2$, NH$_2$ or NMe2 radical;

R1, R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy;

R1 and R2 can form a 5- or 6-membered ring which may or may not have a heteroatom, such as O, S or N;

to their racemates, enantiomers or diastereoisomers and their mixtures, to their tautomers and to their pharmaceutically acceptable salts.

The present invention preferably relates to the pharmaceutical compositions comprising, as active principle, a derivative of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, trifluoromethyl, trifluoromethylsulfanyl, trifluoromethoxy or (1–6C)alkyl;

R5 is a phenyl;

R6 is a chlorine;

R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy; to their isomers, to their mixtures, to their racemates, enantiomers, diastereoisomers or tautomers, and to their pharmaceutically acceptable salts.

The present invention also relates to the use, as medicament, of the aminoindazole derivatives of the formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NR1 radical; these radicals optionally being substituted by 1 or more substituents chosen from CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;

R5 and R6 are, independently of one another, chosen from the following radicals halogen, CN, NO2, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, heterocycle, cycloalkyl, alkenyl, alkynyl, adamantyl or polycycloalkyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R1, R2, R8, R9, R10 and R11 are, independently of one another, a hydrogen, (1–6C)alkyl, aryl, alkenyl, alkynyl, heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl, trifluoromethoxy;

R1 and R2 or R8 and R9 or R10 and R11 can form a 5- or 6-membered ring which may or may not have a heteroatom, such as O, S or N;

and, when R3 is a 6-membered nitrogenous heteroaryl or a thiazolyl or an imidazolyl or an oxazolyl, then at least one of the R5 and R6 groups is an aryl which is optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

to their racemates, enantiomers or diastereoisomers and their mixtures, to their tautomers and to their pharmaceutically acceptable salts.

The present invention relates more particularly to the use, as medicament, of the aminoindazole derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1 or C(=NH)NR1 radical;

these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, oxo, trifluoromethyl, trifluoromethylsulfanyl, trifluoromethoxy or (1–6C)alkyl;

R5 is an aryl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;

R6 is a halogen, methyl, cyclopropyl, CN, OH, methoxy, trifluoromethyl, ethylenyl, acetylenyl, trifluoromethoxy, NO$_2$, NH$_2$ or NMe2 radical;

R1, R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy;

R1 and R2 can form a 5- or 6-membered ring which may or may not have a heteroatom, such as O, S or N;

to their racemates, enantiomers or diastereoisomers and their mixtures, to their tautomers and to their pharmaceutically acceptable salts.

The present invention preferably relates to the use, as medicament, of the aminoindazole derivatives of formula (I) in which:

R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, COOR1, SO$_2$R1, C(=NH)R1 or C(=NH)NR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, formyl, trifluoromethyl, trifluoromethylsulfanyl, trifluoromethoxy or (1–6C)alkyl;

R5 is a phenyl;

R6 is a chlorine;

R1 and R2 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, trifluoromethyl or trifluoromethoxy; to their isomers, to their mixtures, to their racemates, enantiomers, diastereoisomers or tautomers, and to their pharmaceutically acceptable salts.

The derivatives of formula (I) can be obtained from the corresponding 3-amino derivatives (V) for which the nitrogen in the I-position is optionally protected with a group Pr. Pr is a trimethylsilylethoxymethyl, tosyl, mesyl or benzyl radical or the groups known for the protection of the NH groups of aromatic heterocycles as indicated in T. W. Greene, Protective Groups in Organic Synthesis, J. Wiley-Interscience Publication (1999)

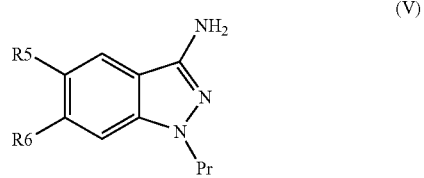

The 3-amino 1H-indazoles of formula (II) can be obtained by reaction of a 2-fluorobenzonitrile with hydrazine hydrate or hydrochloride at reflux for 2 to 18 hours in an alcohol of ethanol or n-butanol type according to R. F. Kaltenbach, Bioorg. Med. Chem. Lett., 9(15), 2259–62 (1999):

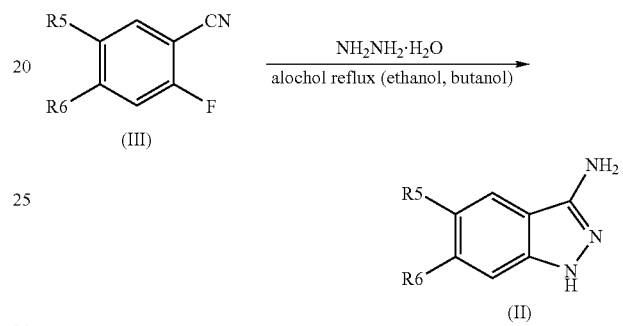

The compounds for which R5 and R6 are, independently of one another, chosen from the following radicals: hydrogen, halogen, CN, NO$_2$, NH$_2$, OH, COOH, C(O)OR8, —O—C(O)R8, NR8R9, NHC(O)R8, C(O)NR8R9, NHC(S)R8, C(S)NR8R9, SR8, S(O)R8, SO$_2$R8, NHSO$_2$R8, SO$_2$NR8R9, —O—SO$_2$R8, —SO$_2$—O—R8, trifluoromethyl, trifluoromethoxy, (1–6C)alkyl, (1–6C)alkoxy, aryl, aryl(1–6C)alkyl, heteroaryl, heteroaryl(1–6C)alkyl, cycloalkyl, alkenyl, alkynyl or adamantyl; these radicals optionally being substituted by 1 or more substituents chosen from halogen, CN, NO$_2$, NH$_2$, OH, OR10, COOH, C(O)OR10, —O—C(O)R10, NR10R11, NHC(O)R10, C(O) NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl; can be obtained by reactions involving the chemistry of palladium: Suzuki (A. Suzuki, Pure Appl. Chem., 63, 419–22 (1991), Stille (J. Stille, Angew. Chem., Int. Ed., 25, 508–24 (1986)), Heck (R. F. Heck, Org. React., 27, 345–90 (1982)), Sonogashira, (K. Sonogashira, Synthesis, 777 (1977)), Buckwald (S. L. Buckwald, Acc. Chem. Re., 31, 805 (1998)), from the corresponding halogenated derivatives.

For this, it is necessary to protect the reactive functional groups. Thus, the OH, SH, COOH and NH$_2$ functional groups must be protected before carrying out the coupling. The protective groups are introduced according to any method known to a person skilled in the art and in particular those described by T. W. Greene, Protective groups in Organic Synthesis, J. Wiley-Interscience Publication (1999). It is preferable to protect the nitrogen in the 1-position with groups such as tert-butoxycarbonyl or silicon derivatives. The choice will preferably be made of a tert-butyldimethylsilyl or triisopropylsilyl silyl group which can be removed by fluoride anions or with acetic acid and more particularly a trimethylsilylethoxymethyl group which can be cleaved by tetrabutylammonium fluoride at reflux in solvents such as tetrahydrofuran or dioxane (J. P. Whitten, J. Org. Chem., 51, 1891 (1986); B. H. Lipshutz, Tetrahedron Lett., 4095 (1986)) or by 2N hydrochloric acid in methanol or ethanol at reflux.

The derivatives protected in the 1-position with trimethylsilylethoxymethyl are obtained by reacting the starting compound with trimethylsilylethoxymethyl chloride in the presence of sodium hydride in a solvent, such as dimethylformamide, at ambient temperature (J. P. Whitten, J. Org. Chem., 51, 1891 (1986); M. P. Edwards, Tetrahedron, 42, 3723 (1986)).

Likewise, the 1-NH nitrogen functional group of the indazole will be protected by groups such as silyl derivatives, benzyl, carbamate or tosyl. For example, in the case where it would be desired to carry out coupling with palladium to a derivative halogenated in the 6-position, it will be necessary to protect the nitrogen in the 1-position as shown below (X=Cl, Br or I):

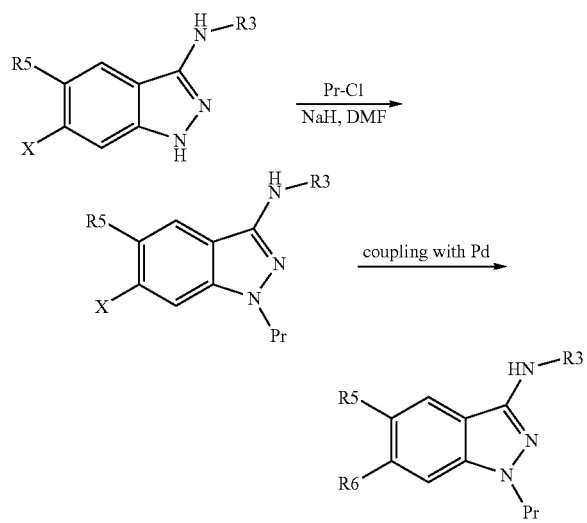

Deprotection is carried out according to methods known to a person skilled in the art and described by T. W. Greene, Protective Groups in Organic Synthesis, J. Wiley-Interscience Publication (1999). For example, if the protective group in the 1-position is a trimethylsilylethoxymethyl, it can be deprotected by reaction with tetrabutylammonium fluoride as shown below:

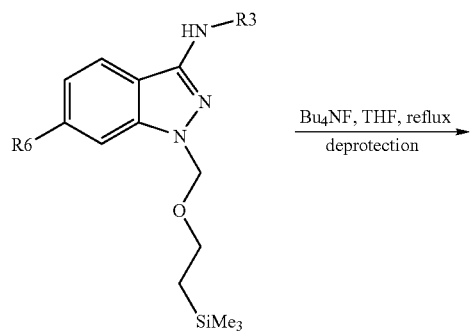

-continued

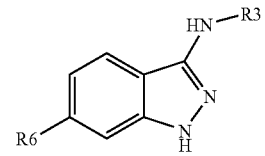

When one of the R5 or R6 groups involved in the coupling using the chemistry of palladium itself comprises a reactive functional group, such as hydroxyl, amine, thiol or acid or generally includes a heteroatom, it is also necessary to protect the latter before carrying out the coupling with palladium. Thus, for example, a phenol functional group will be introduced in the protected form (O-benzyl, for example) from the chlorinated derivative, the nitrogen in the 1-position being protected as explained previously:

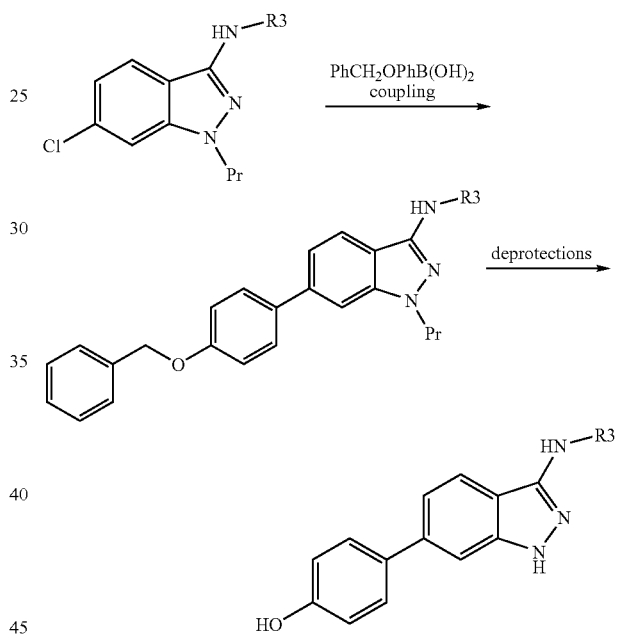

The benzyl group will subsequently be removed, for example by treatment with trimethylsilyl iodide at reflux in acetonitrile. Protection can also be carried out by a trimethylsilylethoxymethyl group which can be cleaved by tetrabutylammonium fluoride at reflux in solvents such as tetrahydrofuran or dioxane. (J. P. Whitten, J. Org. Chem., 51, 1891 (1986); B. H. Lipshutz, Tetrahedron Lett., 4095 (1986)) or by 2N hydrochloric acid in methanol or ethanol at reflux.

When R5 and R6 are, independently of one another, an aryl and a halogen, the aryl functional group is introduced from coupling with palladium to a brominated position, the nitrogen in the 1- and 3-positions being appropriately protected. Preferably, Pr represents a trimethylsilylethoxymethyl and Pr' represents an n-butylcarbonyl group which forms, with the nitrogen, an n-butylamide. The stage of deprotecting the amide is carried out in the presence of ethanolamine at reflux for one week in DMF. This cleavage can also be carried out with stannous chloride in ethanol (R J Griffin, J. Chem. Soc. Perkin I, 1992, 1811–1819) or else sodium methoxide in methanol (Y. Furukawa, Chem. Pharm. Bull., 1968,16, 1076) or any other alkoxide in the corresponding alcohol.

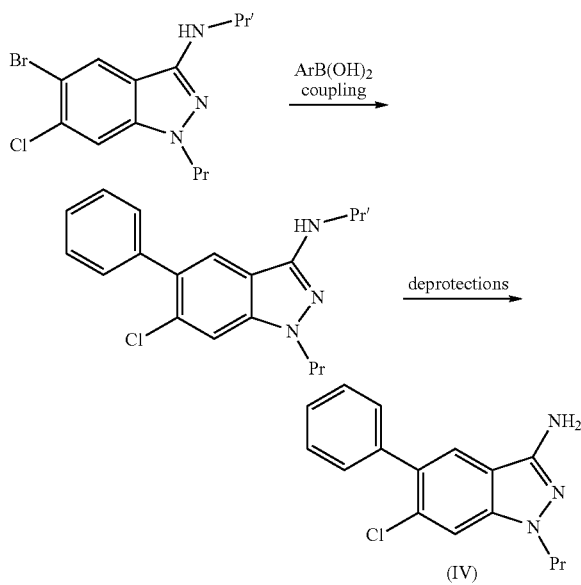

The compounds of formula (II) are the starting point for the preparation of a great variety of products obtained by reaction of the primary amine functional group of the 3-aminoindazole in all the conventional reactions of this functional group, such as: alkylation, acylation, reactions with carbonyl derivatives followed by reduction, sulfonation, conversion to ureas or carbamates, arylation (Castro reaction or Buchwald reaction), and the like.

The reductive aminations or derivatives of general formula (I) where R3 is H when Pr is trimethylsilylethoxymethyl can be carried out using boron derivatives, such as sodium triacetoxyborohydride, in dichloromethane in the presence of an aldehyde of type R1CHO under the conditions described in Organic Reactions, Vol. 59, 1–714 (E. Baxter, A. Reitz), or by the other reducing agents commonly used to reduce imines, to form products where R3 is (1–6C)alkyl, aryl(1–6C)alkyl, heteroaryl(1–6C)alkyl, heterocycloalkyl, cycloalkyl or polycycloalkyl, these radicals optionally being substituted by 1 or more substituents chosen from halogen, CN, $NO_2$, $NH_2$, OH, OR1, COOH, C(O)OR1, —O—C(O)R1, NR1R2, NHC(O)R1, C(O)NR1R2, SR1, S(O)R1, $SO_2$R1, $NHSO_2$R1, $SO_2$NR1R2, C(S)NR1R2, NHC(S)R1, —O—$SO_2$R1, —$SO_2$—O—R1, aryl, heteroaryl, formyl, trifluoromethyl, trifluoromethylsulfanyl, trifluoromethoxy or (1–6C)alkyl.

Condensations of the derivatives of general formula (I) where R3 is H with isocyanates of type OCNR1 can be carried out in particular in tetrahydrofuran and according to the examples described in Comprehensive Organic Functional Group Transformations, Vol. 6 (Katritzky, Meth-Cohn, Rees 1995), to form products where R3 is CONR1R2 and R1, R2, are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, trifluoromethyl or trifluoromethoxy.

Sulfonations of derivatives of general formula (I) where R3 is H can be carried out from a sulfonyl chloride of $R1SO_2Cl$ type in the presence of a base (in particular tertiary amines, such as triethylamine, or aromatic amines, such as pyridine) in a conventional solvent, such as, for example, dichloromethane, to form the products where R3 is $SO_2R1$ and R1 is a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, $NO_2$, $NH_2$, OH, COOH, COOalkyl, $CONH_2$, formyl, trifluoromethyl or trifluoromethoxy.

The compound in IV where Pr is trimethylsilylethoxymethyl is 3-amino-5-phenyl-6-chloro-1-[(2-trimethylsilylethoxy)methyl]indazole and is obtained in the following way:

3-Amino-5-phenyl-6-chloro-1-[(2-trimethylsilylethoxy)methyl]indazole 1.63 cm³ of ethanolamine and then 2.24 g of potassium carbonate are added to 2.4 g of N-[5-phenyl-6-chloro-1-[(2-trimethylsilylethoxy)methyl]indazol-3-yl]butanamide described hereinafter, in 75 cm³ of dimethylformamide and the mixture is heated at reflux for one week. The reaction medium is concentrated to dryness under reduced pressure and taken up in 250 cm³ of ethyl acetate and 100 cm³ of water. The organic phase is separated by settling and washed successively with 2 times 100 cm³ of water and 75 cm³ of sodium chloride solution. The organic phase is dried over magnesium sulfate, filtered and then concentrated to dryness under reduced pressure (2 kPa, 50° C.). The crude oil obtained is purified by chromatography under an argon pressure of 50 kPa on a column of silica gel (particle size 40–60 μm; diameter 4 cm), elution being carried out with a cyclohexane/ethyl acetate (80/20 by volume) mixture and 35 cm³ fractions being collected. The fractions comprising the expected product are combined and evaporated under reduced pressure (2 kPa; 50° C.). After drying (90 Pa; 45° C.), 0.43 g of 3-amino-5-phenyl-6-chloro-1-[(2-trimethylsilylethoxy)methyl]-indazole is obtained in the form of a yellow oil.

¹H N.M.R. spectrum (300 MHz, $(CD_3)_2SO$, δ in ppm): −0.05 (s, 9H), 0.83 (t, J=8 Hz, 2H), 3.52 (t, J=8 Hz, 2H), 5.49 (s, 2H), 5.75 (broad s, 2H), from 7.30 to 7.55 (mt, 5H), 7.77 (s, 1H), 7.81 (s, 1H).

N-[5-Phenyl-6-chloro-1-[(2-trimethylsilylethoxy)methyl]indazol-3-yl]butanamide is obtained in the following way:

821 mg of phenylboronic acid, 1.14 g of sodium carbonate in 30 cm³ of distilled water and, finally, 347 mg of tetrakis(triphenylphosphine)palladium are added to 2 g of N-[5-bromo-6-chloro-1-[(2-trimethylsilylethoxy)methyl]indazol-3-yl]butanamide described hereinafter in 180 cm³ of dioxane. The mixture is heated at reflux for 90 minutes and is then allowed to return to 20° C. in order to add 100 cm³ of ethyl acetate and 100 cm³ of distilled water. The organic phase is washed with 100 cm³ of a saturated aqueous sodium chloride solution, then separated by settling and dried over magnesium sulfate. After filtering through a sintered glass funnel, the filtrate is concentrated to dryness under reduced pressure (2 kPa; 50° C.). The residue is purified by chromatography under an argon pressure of 50 kPa on a column of silica gel (particle size 40–60 μm; diameter 4.5 cm), elution being carried out with a cyclohexane/ethyl acetate (80/20 by volume) mixture and 35 cm³ fractions being collected. The fractions comprising the expected product are combined and evaporated under reduced pressure (2 kPa; 50° C.). After drying, 90 Pa; 45° C.), 2 g of N-[5-phenyl-6-chloro-1-

[(2-trimethylsilylethoxy)methyl]indazol-3-yl]butanamide are thus obtained in the form of a yellow oil.

$^1$H N.M.R. spectrum (300 MHz, (CD$_3$)$_2$SO, δ in ppm): −0.05 (s, 9H), 0.85 (t, J=8 Hz, 2H), 0.92 (t, J=7.5 Hz, 3H), 1.63 (mt, 2H), 2.38 (t, J=7.5 Hz, 2H), 3.56 (t, J=8 Hz, 2H), 5.70 (s, 2H), from 7.30 to 7.55 (mt, 5H), 7.91 (s, 1H), 7.99 (s, 1H), 10.59 (broad s, 1H).

N-[5-Bromo-6-chloro-1-[(2-trimethylsilylethoxy)methyl]indazol-3-yl]butanamide is obtained in the following way:

0.22 cm$^3$ of pyridine is added to 1 g of N-[6-chloro-1-[(2-trimethylsilylethoxy)methyl]indazol-3-yl]butanamide described hereinafter in 15 cm$^3$ of chloroform and then 0.14 cm$^3$ of bromine is added. The mixture is stirred at 20° C. for 24 hours and then 50 cm$^3$ of dichloromethane and 50 cm$^3$ of a saturated aqueous sodium sulfate solution are subsequently added. After stirring for 10 minutes, the insoluble material is removed by filtration through a sintered glass funnel and the organic phase is washed with 50 cm$^3$ of a saturated aqueous sodium chloride solution. The organic phase is separated by settling, dried over magnesium sulfate, filtered and evaporated to dryness under reduced pressure (2 kPa; 45° C.). The residue is purified by chromatography under an argon pressure of 50 kPa on a column of silica gel (particle size 40–60 μm; diameter 3.5 cm), elution being carried out with an ethyl acetate/cyclohexane (20/80 by volume) mixture and 35 cm$^3$ fractions being collected. The fractions comprising the expected product are combined and evaporated under reduced pressure (2 kPa; 50° C.). After drying (90 Pa; 45° C.), 0.94 g of N-[5-bromo-6-chloro-1-[(2-trimethylsilylethoxy)methyl]indazol-3-yl]butanamide is obtained in the form of a white solid melting at 130° C.

$^1$H N.M.R. spectrum (300 MHz, (CD$_3$)$_2$SO, δ in ppm): −0.08 (s, 9H), 0.82 (t, J=8 Hz, 2H), 0.95 (t, J=7.5 Hz, 3H), 1.66 (mt, 2H), 2.40 (t, J=7.5 Hz, 2H), 3.52 (t, J=8 Hz, 2H), 5.66 (s, 2H), 8.13 (s, 1H), 8.34 (s, 1H), 10.67 (broad s, 1H).

N-[6-Chloro-1-[(2-trimethylsilylethoxy)methyl]indazol-3-yl]butanamide is obtained in the following way:

3 g of N-(6-chloro-1H-indazol-3-yl)butanamide, in solution of 40 cm$^3$ of dimethylformamide, are added to 606 mg of 60% sodium hydride in 20 cm$^3$ of dimethylformamide. After having cooled to approximately 5° C., 2.68 cm$^3$ of 2-(trimethylsilyl)ethoxymethyl chloride in 10 cm$^3$ of dimethylformamide are added.

The temperature is allowed to return to approximately 21° C. and the mixture is stirred for 2 hours. The reaction medium is subsequently evaporated under reduced pressure (2 kPa; 45° C.). The residue is taken up in 200 cm$^3$ of ethylacetate and in 100 cm$^3$ of distilled water. Washing is again carried out with 2 times 100 cm$^3$ of distilled water and with 100 cm$^3$ of a saturated aqueous sodium chloride solution. The organic phase is dried over magnesium sulfate, filtered through a sintered glass funnel and then evaporated under reduced pressure (2 kPa; 50° C.). The residue is purified by chromatography under an argon pressure of 50 kPa on a column of silica gel (particle size 40–60 μm; diameter 4.5 cm), elution being carried out with a cyclohexane/ethylacetate (80/20 by volume) mixture and 100 cm$^3$ fractions being collected. The fractions comprising the expected product are combined and evaporated under reduced pressure (2 kPa; 50° C.). After drying (90 Pa; 50° C.), 3 g of N-[6-chloro-1-[(2-trimethylsilylethoxy)methyl]indazol-3-yl]butanamide are obtained in the form of a yellow oil.

$^1$H N.M.R. spectrum (300 MHz, (CD$_3$)$_2$SO, δ in ppm): −0.08 (s, 9H), 0.83 (broad t, J=8 Hz, 2H), 0.96 (t, J=7.5 Hz, 3H), 1.67 (mt, 2H), 2.40 (t, J=7.5 Hz, 2H), 3.53 (t, J=8 Hz, 2H), 5.66 (s, 2H), 7.16 (dd, J=9 to 2 Hz, 1H), 7.86 (d, J=2 Hz, 1H), 7.88 (d, J=9 Hz, 1H), 10.53 (unresolved peak, 1H).

N-(6-Chloro-1H-indazol-3-yl)butanamide 0.47 cm$^3$ of butyryl chloride is added to 750 mg of 3-amino-6-chloro-1H-indazole in 10 cm$^3$ of pyridine after having cooled the reaction medium to approximately 3° C. The medium is then subsequently allowed to return to 19° C. over 14 hours. The reaction medium is evaporated to dryness under reduced pressure (2 kPa; 40° C.). The residue is taken up in 50 cm$^3$ of ethyl acetate, in 50 cm$^3$ of tetrahydrofuran and in 50 cm$^3$ of distilled water. The organic phase is washed again with 50 cm$^3$ of distilled water and with 50 cm$^3$ of a saturated aqueous sodium chloride solution and then dried over magnesium sulfate, filtered through a sintered glass funnel and evaporated under reduced pressure. The residue obtained is purified by chromatography under an argon pressure of 50 kPa on a column of silica gel (particle size 40–60 μm; diameter 2.5 cm), elution being carried out with cyclohexane/ethyl acetate (70/30 by volume) and 25 cm$^3$ fractions being collected. The fractions comprising the expected product are combined and then evaporated under reduced pressure (2 kPa; 40° C.). After drying (90 Pa; 45° C.), 200 mg of N-(6-chloro-1H-indazol-3-yl)butanamide are obtained in the form of a white solid melting at 230° C.

$^1$H N.M.R. spectrum (300 MHz, (CD$_3$)$_2$SO, δ in ppm): 0.98 (t, J=7 Hz, 3H), 1.67 (mt, 2H), 2.40 (t, J=7 Hz, 2H), 7.08 (dd, J=9 and 2 Hz, 1H), 7.52 (d, J=2 Hz, 1H), 7.84 (d, J=9 Hz, 1H), 10.39 (unresolved peak, 1H), from 12.50 to 13.00 (broad unresolved peak, 1H).

3-Amino-6-chloro-5-phenyl-1H-indazole is obtained from 3-amino-5-phenyl-6-chloro-1-[(2-trimethylsilylethoxy)methyl]indazole.

300 μl of 2N HCl are added to 108.3 mg of the compound 3-amino-5-phenyl-6-chloro-1-[(2-trimethylsilylethoxy)methyl]indazole in 4.7 ml of methanol. The reaction is placed under microwaves at 140° C. for 150 seconds.

The mixture is poured onto a saturated KH$_2$PO$_4$ solution and extraction is carried out with AcOEt. The organic phases are dried over anhydrous MgSO$_4$, filtered and concentrated. The crude product obtained is purified through silica and 63.5 mg of the compound 3-amino-6-chloro-5-phenyl-1H-indazole are obtained.

The compounds of formula (I) are isolated and can be purified by the usual known methods, for example by crystallization, chromatography or extraction.

The compounds of formula (I) can optionally be converted to addition salts with an inorganic or organic acid by the action of such an acid in an organic solvent, such as an alcohol, ketone, an ether or a chlorinated solvent. These salts also form part of the invention.

Mention may be made, as examples of pharmaceutically acceptable salts, of the following salts: benzenesulfonate, hydrobromide, hydrochloride, citrate, ethanesulfonate, fumarate, gluconate, iodate, maleate, isethionate, methanesulfonate, methylenebis-β-oxynaphthoate, nitrate, oxalate, pamoate, phosphate, salicylate, succinate, sulfate, tartrate, theophyllineacetate and p-toluenesulfonate.

The compounds of formula (I) are kinase inhibitors and are thus of use in the prevention and treatment of neurodegenerative diseases, Alzheimer's disease, Parkinson's disease, frontoparietal dementia, corticobasal degeneration, Pick's disease, strokes, cranial and spinal traumas and peripheral neuropathies, obesity, essential hypertension, atherosclerotic cardiovascular diseases, polycystic ovaries syndrome, syndrome X, immunodeficiency and cancer.

The activities were determined by measuring the inhibition of the phosphorylation of the tau protein in adult rat cortex sections.

Cortex sections with a thickness of 300 μm are prepared from male OFA rats (Iffa-Credo) aged 8–10 weeks, sacrificed by decapitation. They are incubated in 5 ml of DMEM medium comprising pyruvate and glucose 4.5 g/l at 37° C. for 40 min. The sections are subsequently washed twice with the medium, distributed in microtubes (50 μl in 500 μl of medium, with or without test compounds) and incubated at 37° C. with stirring. Two hours later, the experiment is halted by centrifuging. The sections are lyzed, sonicated and centrifuged at 18300 g for 15 min at 4° C. The concentration of proteins in the supernatant is determined by a commercial assay (BCA Protein Assay, Pierce) based on the Lowry method.

The samples, denatured beforehand at 70° C. for 10 min, are separated on 4–12% Bis-tris vertical gel in the presence of MOPS-SDS buffer and are electrotransferred onto a nitrocellulose membrane. Immunolabeling is carried out with the monoclonal antibody AD2, which specifically recognizes the Ser396/404 phosphorylated epitopes of the tau protein. The immunoreactive proteins are visualized by addition of a second antibody directed against mouse IgGs and coupled to peroxidase and of a chemoluminescent substrate: The autoradiograms obtained are finally quantified using the 'GeneTools' software from Syngene (GeneGnome, Ozyme) to determine an $IC_{50}$ value.

The compounds of formula (I) exhibit a highly advantageous activity and in particular some compounds have an $IC_{50}$ value of less than 100 μM.

The conditions for analysis of the products by LC/MS were produced on a Waters Alliance 2695 device for the LC part and a Waters-Micromass Platform II for the mass part.

The following examples illustrate the invention without implied limitation.

EXAMPLE A1

N-butyl-6-chloro-5-phenyl-1H-indazol-3-amine

Stage 1: 24 mg of n-butyraldehyde and 113 mg of sodium triacetoxyborohydride are added to a solution of 100 mg of 3-amino-5-phenyl-6-chloro-1-[(2-trimethylsilylethoxy)methyl]indazole in 5 cm³ of methylene chloride. After 3 hours at ambient temperature, the reaction medium is hydrolyzed and then extracted with methylene chloride. The organic phase is dried over magnesium sulfate, filtered and evaporated. Purification of the crude product by chromatography on silica (eluent: ethylacetate/hexane (80/20, v/v)) makes it possible to obtain 21 mg of butyl[6-chloro-5-phenyl-1-(2-(trimethylsilanyl)ethoxymethyl-1H-indazol-3-yl]amine (yellow solid).

Mass spectrum: 432 [M+H]⁺; retention time: 5.26 minutes. ¹H NMR [$d_6$-DMSO]: 7.83 (1H, s), 7.73 (1H, s), 7.35–7.50 (5H, m), 6.25 (1H, t, J=6 Hz), 5.49 (2H, s), 3.52 (2H, t, J=8 Hz), 3.24 (2H, m), 1.60 (2H, m), 1.39 (2H, m), 0.91 (3H, t, J=7 Hz), 0.81 (2H, t, J=8 Hz), −0.07 (9H, s).

Stage 2: 0.7 ml of 2N HCl is added to a solution of 21 mg of butyl[6-chloro-5-phenyl-1-(2-(trimethylsilyl)ethoxymethyl)-1H-indazol-3-yl]amine in 0.3 cm³ of methanol. The reaction medium is stirred at ambient temperature for 48 hours and at reflux for 1 hour, then evaporated. The solid obtained is dried under vacuum to give 16 mg of N-butyl-6-chloro-5-phenyl-1H-indazol-3-amine (yellow solid).

Mass spectrum: 300[M+H]⁺; retention time: 4.25 minutes. ¹H NMR [$d_6$-DMSO]: 7.52 (1H, s), 7.95(1H, s), 7.35–7.50 (5H, m), 3.30 (2H, t, J=7 Hz), 1.61 (2H, m), 1.40 (2H, m), 0.92 (3H, t, J=7 Hz).

EXAMPLE A2

3-(6-Chloro-5-phenyl-1H-indazol-3-ylamino)thiophene-2-carbonitrile 38 mg of 2-dicyclohexylphosphino-2'-(N,N-dimethylamino)biphenyl, 20 mg of $Pd_2dba_3$ (tris(dibenzylideneacetone)dipalladium(0)), 52 mg of 2-cyano 3-bromo thiophene and 23 mg of sodium tert-butoxide are added to 52 mg of the compound 3-amino-5-phenyl-6-chloro-1-[(2-trimethylsilylethoxy)methyl]indazole in 0.5 ml of NMP (1-methyl-2-pyrrolidone).

The reaction is placed under microwaves at 140° C. for 3 min. After the usual treatments, the crude product is treated with 2N HCl in methanol to give, after purification, 8.4 mg of 3-(6-chloro-5-phenyl-1H-indazol-3-ylamino)thiophene-2-carbonitrile.

Mass spectrum: 351[M+H]⁺; retention time: 4.19 minutes. ¹H NMR [$d_6$-DMSO]: 7.40 (1H, m), 7.48 (2H, m), 7.53 (3H, m), 7.81 (1H, s), 8.09 (1H, s), 8.27 (1H, d, J=5.5 Hz), 8.91 (2H, s).

EXAMPLES A3 TO A5

The examples below were obtained in a way equivalent to A2.

| N° | Name | Starting material | Retention time/ [M + H]⁺ | NMR $d_6$-DMSO, unless otherwise indicated |
|---|---|---|---|---|
| A3 | (6-Chloro-5-phenyl-1H-indazol-3-yl)(pyridin-2-yl)amine | 2-bromo-pyridine | 2.89/321 | 7.07 ppm(b, 1H), from 7.36 ppm to 7.50 ppm(m, 5H), 7.55 ppm(b, 1H), 7.67 ppm(s, 1H), 7.87 ppm (s, 1H), 7.95 ppm(1, 1H), 8.21 ppm (b, 1H) in MeOD |
| A4 | (6-Chloro-5-phenyl-1H-indazol-3-yl)(5-nitropyridin-2-yl)amine | 2-bromo-5-nitro-pyridine | 4.58/366 | from 7.42 to 7.52 ppm(m, 5H), 7.63 ppm(s, 1H), 7.65 ppm(s, 1H), 7.94 ppm(d, J = 9 Hz, 1H), 8.43 ppm (dd, J = 2.5 and 9 Hz, 1H), 9.13 ppm(d, J = 2.5 Hz, 1H), 7.77 ppm (bs, 1H), 9.55 ppm(bs, 1H) |
| A5 | (6-Chloro-5-phenyl-1H-indazol-3-yl)(6- | 2-bromo-6- | | 3.87 ppm(s, 3H), 6.31 ppm(d, J = 7.5 Hz, 1H), 7.36 ppm(bd, J = 7.5 Hz, 1H), from 7.35 to 7.50 ppm |

| N° | Name | Starting material | Retention time/ [M + H]+ | NMR d6-DMSO, unless otherwise indicated |
|---|---|---|---|---|
| | methoxypyridin-2-yl)amine | methoxy pyridine | | (m, 5H), 7.36 ppm(t, J = 7.5 Hz, 1H), 7.54 ppm(s, 1H), 7.69 ppm(bs, 1H) in CDCl₃ |

EXAMPLE B1

N-(6-chloro-5-phenyl-1H-indazol-3-yl)-N'-phenylurea

Stage 1: 39 μl of phenyl isocyanate are added to a solution of 102.2 mg of 3-amino-5-phenyl-6-chloro-1-[(2-trimethylsilylethoxy)methyl]indazole in 2.5 cm³ of tetrahydrofuran. The reaction medium is stirred at ambient temperature for 24 hours and is then evaporated. Purification of the crude product by chromatography on silica (eluant: methylene chloride/acetone (98/2, v/v)) makes it possible to obtain 122.5 mg of 1-[6-chloro-5-phenyl-1-(2-trimethylsilanylethoxymethyl)-1H-indazol-3-yl]-3-phenylurea (colorless solid).

Mass spectrum: 493[M+H]⁺; retention time: 6.02 minutes. ¹H NMR [d₆-DMSO]: 9.89 (1H, broad s), 9.86(1H, broad s), 8.20 (1H, s), 8.07 (1H, s), 7.35–7.50 (5H, m), 5.81 (2H, s), 3.66 (2H, t, J=8 Hz), 0.92 (2H, t, J=8 Hz), −0.12 (9H, s).

Stage 2: 1 ml of 2N HCl is added to a solution of 106 mg of 1-[6-chloro-5-phenyl-1-(2-trimethylsilanylethoxymethyl)-1H-indazol-3-yl]-3-phenylurea in 12 cm³ of methanol. The reaction medium is stirred at ambient temperature for 48 hours and at reflux for 5 hours, then evaporated. The solid obtained is dried under vacuum to give 82 mg of N-(6-chloro-5-phenyl-1H-indazol-3-yl)-N'-phenylurea (colorless solid).

Mass spectrum: 363 [M+H]⁺; retention time: 5.15 minutes. ¹H NMR [d₆-DMSO]: 12.64 (1H, broad s), 9.70(1H, broad s), 9.59 (1H, broad s), 8.07 (1H, s), 7.64 (1H, s), 7.50 (7H, m), 7.30 (2H, m), 7.0 (1H, m).

EXAMPLE B2

1-(6-Chloro-5-phenyl-1H-indazol-3-yl)-3-(4-ethoxyphenyl)urea 36.4 mg of 4-ethoxyphenyl isocyanate are added to 80 mg of 3-amino-5-phenyl-6-chloro-1-[(2-trimethylsilylethoxy)methyl]indazole in 1 ml of THF. The mixture is heated at 50° C. for 1 h and is then hydrolyzed in a saturated KH₂PO₄ solution and extracted with methylene chloride. After drying and evaporating, the crude product is purified by chromatography on silica with an AcOEt/hexane mixture. The product obtained is deprotected in 2 ml of a 1/1 MeOH/2N HCL mixture at reflux for 3 h. 62.5 mg of 1-(6-chloro-5-phenyl-1H-indazol-3-yl)-3-(4-ethoxyphenyl)urea are obtained.

Mass spectrum: 407 [M+H]⁺; retention time: 4.36 minutes ¹H NMR [d₆-DMSO]: 1.3 (3H, t, J=7 Hz), 3.98 (2H, q, J=7 Hz), 6.87 and 7.36 (AA'-BB', 4H), 7.36–7.50 (5H, m), 7.63 (1H, s), 8.08 (1H, s), 9.53 (2H, s), 12.53 (1H, s)

EXAMPLES B3 TO B12

The products B3 to B12 are obtained in a way equivalent to the product B2

| N° | Name | Starting material | Retention time/ [M + H]+ | NMR d6-DMSO |
|---|---|---|---|---|
| B3 | 1-(6-Chloro-5-phenyl-1H-indazol-3-yl)-3-(3,4-dichlorophenyl)urea | 3,4-dichlorophenyl isocyanate | 4.75/407 [M − H] | from 7.38 to 7.48 ppm(m, 6H), 7.53 ppm(d, J = 8.5 Hz, 1H), 7.66 ppm(s, 1H), 7.90 ppm (d, J = 2.5 Hz, 1H), 8.01 ppm (s, 1H), 9.70 ppm(s, 1H), 9.84 ppm(s, 1H), 12.72 ppm(bs, 1H) |
| B4 | 3-[3-(6-Chloro-5-phenyl-1H-indazol-3-yl)-ureido]-propionic acid methyl ester | Phenethyl isocyanate | 3.71/373 | 2.56 ppm(t, J = 6.5 Hz, 2H), 3.44 ppm(m, 2H), 3.61(s, 3H), from 7.36 to 7.50 ppm(m, 5H), 7.58 ppm(s, 1H), 7.81(b, 1H), 8.08 ppm(s, 1H), 9.48 ppm(s, 1H), 12.52 ppm(bs, 1H) |
| B5 | 1-(6-Chloro-5-phenyl-1H-indazol-3-yl)-3-(4-(dimethylaminophenyl)urea | 4-(dimethylamino)phenyl isocyanate | 3.26/406 | 3.10 ppm(s, 6H), from 7.38 to 7.50 ppm(m, 5H), 7.64(b, 4H), 7.66 ppm(s, 1H), 8.03 ppm(s, 1H), 9.70 ppm(s, 1H), 9.95 ppm(s, 1H), 12.72 ppm (bs, 1H) |
| B6 | 1-(6-Chloro-5-phenyl-1H-indazol-3-yl)-3-isopropylurea | Isopropyl isocyanate | 3.95 329 | 1.16 ppm(d, J = 6.5 Hz, 6H), 3.85 ppm(m, 1H), from 7.38 to 7.50 ppm(m, 5H), 7.58 ppm (b, 1H), 7.60 ppm(s, 1H), 8.10 |

-continued

| N° | Name | Starting material | Retention time/ [M + H]+ | NMR d6-DMSO |
|---|---|---|---|---|
| | | | | ppm(s, 1H), 9.36 ppm(s, 1H), 12.48 ppm(bs, 1H) |
| B7 | 1-(6-Chloro-5-phenyl-1H-indazol-3-yl)-3-cyclohexylurea | Cyclohexyl isocyanate | 4.37/369 | from 1.3 to 1.9 ppm(m, 10H), 3.58 ppm(m, 1H), from 7.38 to 7.49 ppm(m, 5H), 7.57 ppm (s, 1H), 7.68 ppm(bd, J = 5.5 Hz, 1H), 8.10 ppm(s, 1H), 9.38 ppm(s, 1H), 12.48 ppm (bs, 1H) |
| B8 | 1-(6-Chloro-5-phenyl-1H-indazol-3-yl)-3-(3-(trifluoromethyl)phenyl)urea | 3-(Trifluoromethylphenyl isocyanate | 4.61/431 | 7.34 ppm(bd, J = 8 Hz, 1H), from 7.38 ppm to 7.49 ppm(m, 5H), 7.53 ppm(t, J = 8 Hz, 1H), 7.66 ppm(s, 1H), 7.69 ppm (bd, J = 8 Hz, 1H), 7.98 ppm (bs, 1H), 8.03 ppm(s, 1H), 9.71 ppm(s, 1H), 9.96 ppm(s, 1H), 12.76 ppm(bs, 1H) |
| B9 | 1-(6-Chloro-5-phenyl-1H-indazol-3-yl)-3-(2-(thiophen-2-yl)ethyl)urea | 2-(Thiophen-2-yl)ethyl isocyanate | 4.2/397 | 3.02 ppm(t, J = 7 Hz, 2H), 3.46 ppm(m, 2H), 6.92 ppm(dd, J = 1.5 and 3.5 Hz, 1H), 6.95 ppm (dd, J = 3.5 and 5 Hz, 1H), 7.32 ppm(dd, J = 1.5 and 5 Hz, 1H), from 7.37 to 7.49 ppm(m, 5H), 7.58 ppm(s, 1H), 7.80 ppm (bt, J = 6 Hz, 1H), 8.08 ppm(s, 1H), 9.50 ppm(s, 1H), 12.48 ppm(bs, 1H) |
| B10 | (1,3-Benzodioxol-5-yl)-3-(6-chloro-5-phenyl-1H-indazol-3-yl)urea | 1,3-Benzodioxol-5-yl isocyanate | 4.19/407 | 5.97 ppm(s, 2H), 6.81 ppm (dd, J = 2.5 and 8.5 Hz, 1H), 6.84 ppm(d, J = 8.5 Hz, 1H), 7.22 ppm(d, J = 2.5 Hz, 1H), from 7.35 to 7.50 ppm(m, 5H), 7.65 ppm(s, 1H), 8.05 ppm(s, 1H), 9.56 ppm(s, 1H), 9.6 ppm (s, 1H), 12.65(bs, 1H) |
| B11 | 1-(6-Chloro-5-phenyl-1H-indazol-3-yl)-3-(3,5-dimethyl-isoxazol-4-yl)-urea | 3,5-Dimethyl-isoxazol-4-yl isocyanate | 3.76/382 | 2.13 ppm(s, 3H), 2.29 ppm (s, 3H), from 7.36 to 7.50 ppm(m, 5H), 7.64 ppm(s, 1H), 8.03 ppm(s, 1H), 8.75 ppm(s, 1H), 9.74 ppm(s, 1H), 12.68 ppm (bs, 1H) |
| B12 | 1-Benzyl-3-(6-chloro-5-phenyl-1H-indazol-3-yl)-urea | Benzyl isocyanate | 4.2/377 | 4.43 ppm(d, J = 6 Hz, 2H), from 7.20 to 7.50 ppm(m, 10H), 7.58 ppm(s, 1H), 8.10 ppm(bs, 2H), 9.57 ppm(s, 1H), 12.50 ppm(s, 1H) |
| B13 | 1-(6-Chloro-5-phenyl-1H-indazol-3-yl)-3-(phenethyl)thiourea | Phenethyl isothiocyanate | | 2.96 ppm(t, J = 7.0 Hz, 2H), 3.86 ppm(dt, J = 5.5 and 7.0 Hz, 2H), from 7.15 to 7.35 ppm(m, 5H), from 7.35 to 7.50 ppm(m, 5H), 7.64 ppm,(s, 1H), 8.37 ppm(s, 1H), 10.14 ppm(t, J = 5.5 Hz, 1H), 10.97 ppm(s, 1H), 12.73 ppm(s, 1H) |

EXAMPLE C1

1-(6-Chloro-5-phenyl-1H-indazol-3-yl)-3-[3-(4-methylpiperazin-1-yl)propyl]urea

Stage 1: 62 μl of pyridine and 125 μl of ethyl chloroformate are successively added to 387.8 mg of 3-amino-5-phenyl-6-chloro-1-[(2-trimethylsilylethoxy)methyl]indazole in 2 ml of methylene chloride. The reaction is completed after 75 nm. After hydrolysis, extraction and evaporation, 571 mg of crude carbamate, (6-chloro-5-phenyl-1H-indazol-3-yl)carbamic acid ethyl ester, are obtained.

Stage 2: 377 mg of 4-(3-aminopropyl)-1-methylpiperazine are added to 106 mg of the preceding carbamate in 2.5 ml of trifluorotoluene and the reaction is carried out under microwave radiation at 200° C. for 20 min. After purifying by preparative LC/MS (acetonitrile/pH=9 buffer), 60 mg of 1-[6-chloro-5-phenyl-1-(2-trimethylsilanyl)ethoxymethyl)-1H-indazol-3-yl]-3-[3-(4-methylpiperazin-1-yl)propyl]urea are obtained.

Stage 3: The preceding compound is taken up in 2 ml of a 1/1 MeOH/2N HCl mixture and is brought to reflux for 3 h.

$^1$H NMR [d$_6$-DMSO]: 1.63 (2H, m), 2.18 (3H, s), 2.33 (10H, m), 3.21 (2H, m), 7.36–7.48 (5H, m), 7.58 (1H, s), 7.66 (1H, t, J=5.5 Hz), 8.08 (1H, s), 9.37 (1H, s), 12.70 (1H, s).

EXAMPLES C2 TO C19

The products C2 to C19 are obtained in a way equivalent to the product C1

| N° | Name | Starting material | Retention time/ [M + H]$^+$ | NMR d$_6$-DMSO |
|---|---|---|---|---|
| C2 | 1-(6-Chloro-5-phenyl-1H-indazol-3-yl)-3-(3-(imidazol-1-yl)propyl)urea | 3-(Imidazol-1-yl)propylamine | 3/395 | 2.05 ppm(m, 2H), 3.24 ppm(m, 2H), 4.25 ppm (t, J = 6 Hz, 2H), from 7.38 to 7.49 ppm(m, 5H), 7.61 ppm(s, 1H), 7.69 ppm(bs, 1H), 7.76 ppm(d, J = 5.5 Hz, 1H), 7.83 ppm(bs, 1H), 8.08 ppm(s, 1H), 9.19 ppm(s, 1H), 9.53 ppm(s, 1H), 12.53 ppm(bs, 1H) |
| C4 | 1-(6-Chloro-5-phenyl-1H-indazol-3-yl)-3-(2-hydroxy-ethyl)urea | Ethanol-amine | 3.36/331 | 3.27 ppm(m, 2H), 3.49 ppm(t, J = 6.5 Hz, 2H), from 7.38 to 7.50 ppm (m, 5H), 7.59 ppm(s, 1H), 7.83 ppm(b, 1H), 8.10 ppm(s, 1H), 9.49 ppm(s, 1H), 12.50 ppm (bs, 1H) |
| C5 | 1-(6-Chloro-5-phenyl-1H-indazol-3-yl)-3-[3-(4-methylpiperazin-1-yl)propyl]urea | 3-(4-Methyl-piperazin-1-yl)propylamine | 2.52/427 | |
| C6 | Pyrrolidine-1-carboxylic acid (6-chloro-5-phenyl-1H-indazol-3-yl)amide | Pyrrolidine | 4/340 | 1.84 ppm(m, 4H), 3.37 ppm(m, 4H), from 7.37 to 7.49 ppm(m, 5H), 7.61 ppm(s, 1H), 7.72 ppm(s, 1H), 8.80 ppm(s, 1H), 12.62 ppm(s, 1H) |
| C7 | (6-Chloro-5-phenyl-1H-indazol-3-yl)carbamic acid methyl ester | Methyl chloroformate | 4.1/302 | 3.66 ppm(s, 3H), from 7.33 ppm to 7.49 ppm (m, 5H), 7.65 ppm(s, 1H), 7.78 ppm(s, 1H), 10.1 ppm(s, 1H), 12.80 ppm(s, 1H) |
| C8 | (6-Chloro-5-phenyl-1H-indazol-3-yl)urea | Aqueous Ammonia | 3.39/287 | 6.89 ppm(bs, 2H), from 7.37 ppm to 7.49 ppm (m, 5H), 7.59 ppm(s, 1H), 8.09 ppm(s, 1H), 9.37 ppm(s, 1H), 12.51 ppm(bs, 1H) |
| C9 | (6-Chloro-5-phenyl-1H-indazol-3-yl)carbamic acid benzyl ester | Benzyl chloroformate | 4.5/378 | 5.14 ppm(s, 2H), from 7.29 to 7.49 ppm(m, 10H), 7.65 ppm(s, 1H), 7.76 ppm(s, 1H), 10.08 ppm(bs, 1H), 10.77 ppm (bs, 1H) |
| C10 | (6-Chloro-5-phenyl-1H-indazol-3-yl)carbamic acid allyl ester | Allyl chloroformate | 4.4/328 | 4.61 ppm(dl, J = 5 Hz, 2H), 5.21 ppm(dl, H = 11 Hz, 1H), 5.34 ppm (dl, J = 17.5 Hz, 1H), 5.96 ppm(m, 1H), from 7.39 to 7.49 ppm(m, 5H), 7.65 ppm(s, 1H), 7.78 ppm(s, 1H), 10.06 ppm (bs, 1H), 12.76 ppm(bs, 1H) |
| C11 | (6-Chloro-5-phenyl-1H-indazol-3-yl)carbamic acid isobutyl ester | Isobutyl chloroformate | 4.55/344 | 0.90 ppm(d, J = 6.5 Hz, 6H), 1.90 ppm(m, 1H), 3.86 ppm(d, J = 6.5 Hz, 2H), from 7.38 ppm to 7.49 ppm(m, 5H), 7.66 ppm(s, 1H), 7.79 ppm(s, 1H), 9.93 ppm(bs, 1H), 12.93 ppm(bs, 1H) |
| C12 | Piperidine-1-carboxylic acid(6-chloro-5-phenyl- | Piperidine | 3.92/355 | 1.40 ppm(m, 4H), 1.60 ppm(m, 2H), 3.43 ppm (m, 4H), from 7.37 ppm |

-continued

| N° | Name | Starting material | Retention time/ [M + H]+ | NMR d6-DMSO |
|---|---|---|---|---|
| | 1H-indazol-3-yl)-amide | | | to 7.50 ppm(m, 5H), 7.61 ppm(s, 1H), 7.62 ppm(s, 1H), 9.07 ppm(s, 1H), 12.62 ppm(s, 1H) |
| C13 | 1-(3-(Azetidin-1-yl)propyl)-3-(6-chloro-5-phenyl-1H-indazol-3-yl)-urea | Azetidine (double addition) | | 1.50 ppm(m, 2H), 2.02 ppm(m, 1H), 3.20 ppm (m, 2H), 2.54 ppm (masked, 2H), 3.27 ppm (masked, 4H), from 7.35 ppm to 7.50 ppm(m, 5H), 7.59 ppm(s, 1H), 7.72 ppm(bt, J = 6 Hz, 1H), 8.09 ppm(s, 1H), 9.44 ppm(s, 1H), 12.50 ppm(s, 1H) |
| C14 | 1-(6-Chloro-5-phenyl-1H-indazol-3-yl)-3-(3-chloro-propyl)urea | Azetidine (HCL opening) | 4.26/363 | 1.94 ppm(m, 2H), 3.30 ppm(masked, 2H), 3.60 ppm(t, J = 6.5 Hz, 2H), from 7.38 ppm to 7.50 ppm(m, 5H), 7.58 ppm (s, 1H), 7.60 ppm(bt, J = 6 Hz, 1H), 8.07 ppm (s, 1H), 9.40 ppm(s, 1H), 12.41 ppm(s, 1H) |
| C15 | 1-(6,7-Difluoro-5-phenyl-1H-indazol-3-yl)-3-(3-(imidazol-1-yl)propyl)urea | 3-(Imidazol-1-yl)propylamine | | 1.94 ppm(m, 2H), 3.18 ppm(q, J = 6.5 Hz, 2H), 4.02 ppm(t, J = 6.5 Hz, 2H), 6.89 ppm(s, 1H), 7.21 ppm(s, 1H), 7.42 ppm(bt, J = 7.5 Hz, 1H), 7.50 ppm(bt, J = 7.5 Hz, 2H), 7.55 ppm(bd, J = 7.5 Hz, 2H), 7.65 ppm(s, 1H), 7.73 ppm(bt, J = 6.5 Hz, 1H), 8.05 ppm (d, J = 6.0 Hz, 1H), 9.58 ppm(s, 1H) |
| C16 | 1-(3-Amino-propyl)-3-(6-chloro-5-phenyl-1H-indazol-3-yl)urea | 3-Aminopropyl-amine | 2.74/344 | 1.77 ppm(m, 2H), 2.81 ppm(m, 2H), 3.28 ppm (m, 2H), from 7.38 ppm to 7.50 ppm(m, 5H), 7.60 ppm(s, 1H), 7.81 ppm (m, 3H), 8.08 ppm(s, 1H), 9.54 ppm(s, 1H), 12.54 ppm(s, 1H) |
| C17 | 1-(6-Chloro-5-phenyl-1H-indazol-3-yl)-3-[4-(4-(pyridin-3-yl)imidazol-1-yl)butyl]urea | 4-(4-(Pyridin-3-yl)imidazol-1-yl)butylamine | 2.95/486 | 1.51 ppm(m, 2H), 1.90 ppm(m, 2H), 3.26 ppm (m, 2H), 4.23 ppm(t, J = 7 Hz, 2H), from 7.37 ppm to 7.49 ppm(m, 5H), 7.58 ppm(s, 1H), 7.75 ppm(m, 2H), 8.08 ppm (s, 1H), 8.37 ppm(d, J = 2 Hz, 1H), 8.47 ppm (m, 1H), 8.69 ppm(dd, J = 1.5 and 5 Hz, 1H), 9.00 ppm(bs, 1H), 9.12 ppm(d, J = 2 Hz, 1H), 9.48 ppm(s, 1H), 12.40 ppm(bs, 1H) |
| C18 | 1-(6-Chloro-5-phenyl-1H-indazol-3-yl)-3-(2-(pyrrolidin-1-yl)ethyl)urea | 2-(Pyrrolidin-1-yl)ethylamine | 2.8/384 | 1.83 ppm(m, 2H), 1.99 ppm(m, 2H), 3.03 ppm(m, 2H), 3.28 ppm(m, 2H), 3.56 ppm(masked, 4H), from 7.36 ppm to 7.49 ppm(m, 5H), 7.61 ppm(s, 1H), 7.80 ppm(bt, J = 5.5 Hz, 1H), 8.08 ppm(s, 1H), 9.65 ppm(s, 1H), 10.02 ppm(bs, 1H), 12.62 ppm(bs, 1H) |
| C19 | 2,5-Dimethyl-pyrrolidine-1-carboxylic acid(6-chloro-5-phenyl- | 2,5-Dimethyl-pyrrolidine | 4.08/369 | 1.10 and 1.21 ppm(d, J = 7 Hz, 6H), 1.50 and 1.61 ppm(m, 2H), 1.99 and 2.12 ppm(m, 2H), |

| N° | Name | Starting material | Retention time/ [M + H]+ | NMR d6-DMSO |
|---|---|---|---|---|
| | 1H-indazol-3-yl)amide | | | 4.03 and 4.15 ppm(m, 2H), from 7.36 to 7.49 ppm(m, 5H), 7.60 ppm (s, 1H), 7.67 and 7.69 ppm(s, 1H), 8.52 and 8.66 ppm(s, 1H), 12.60 ppm(bs, 1H) |

EXAMPLE D1

N-(6-Chloro-5-phenyl-1H-indazol-3-yl)acetamidine 33 mg of methyl acetimidate are added to 50 mg of 3-amino-6-chloro-5-phenyl-1H-indazole in 3 ml of acetonitrile and 12 mg of acetic acid. The reaction is placed under microwave radiation at 180° C. for 5 min. After the usual treatments and purification through silica, 35 mg of N-(6-chloro-5-phenyl-1H-indazol-3-yl)acetamidine are obtained.

EXAMPLES D2 TO D4

The products below were obtained in a way equivalent to D1.

| N° | Name | Starting material | Retention time/ [M + H]+ | NMR |
|---|---|---|---|---|
| D2 | N-(6-Chloro-5-phenyl-1H-indazol-3-yl)-6-methoxypyrazine-2-carboxamidine | Ethyl 6-methoxy-pyrazine-2-carboximidate | 3.61/379 | 4.08 ppm(s, 3H), from 7.40 to 7.50 ppm (m, 5H), 7.68 ppm(s, 1H), 7.93 ppm(s, 1H), 8.24 ppm(bs, 1H), 8.43 ppm(s, 1H), 8.69 ppm (bs, 1H), 9.27 ppm(s, 1H), 12.80 ppm(bs, 1H) |
| D3 | N-(6-Chloro-5-phenyl-1H-indazol-3-yl)-benzamidine | Ethyl benzimidate | 3.42/347/ | from 7.36 ppm to 7.50 ppm(m, 8H), 7.64 ppm (s, 1H), 7.80 ppm(s, 1H), 8.12 ppm(m, 2H), 8.24 ppm(bs, 1H), 8.76 ppm(bs, 1H), 12.60 ppm (bs, 1H) |
| D4 | N-(6-Chloro-5-phenyl-1H-indazol-3-yl)-pyridine-2-carboxamidine | Ethyl pyridine-2-carboximidate | | From 7.35 to 7.50 ppm (m, 5H), 7.54 ppm(dd, J = 5.0 and 7.5 Hz, 1H), 7.67 ppm(s, 1H), 7.87 ppm(s, 1H), 7.94 ppm (dt, J = 1.5 and 7.5 Hz, 1H), 8.30 ppm(bs, 1H), 8.58 ppm(d, J = 7.5 Hz, 1H), 8.64 ppm(bs, 1H), 8.58 ppm(dd, J = 1.5 and 5.0 Hz, 1H), 12.70 ppm(bs, 1H) |

EXAMPLE E1

N-(6-Chloro-5-phenyl-1H-indazol-3-yl)-3-methoxybenzenesulfonamide

Stage 1: 0.236 cm³ of pyridine and 26.5 mg of 3-methoxyphenylsulfonyl chloride are added to a solution of 54.1 mg of 3-amino-5-phenyl-6-chloro-1-[(2-trimethylsilylethoxy)methyl]indazole in 2 ml of methylene chloride. The reaction medium is stirred at ambient temperature for 24 hours and then evaporated. The purification of the crude product by chromatography on silica (eluent: methylenechloride/acetone (98/2, v/v)) makes it possible to obtain 70 mg of 1N-[6-chloro-5-phenyl-1-(2-(trimethylsilanyl)ethoxymethyl)-1H-indazol-3-yl]-3-methoxybenzenesulfonamide (colorless foam).

Mass spectrum: 546[M+H]+; retention time: 4.24 minutes. ¹H NMR [d6-DMSO]: 10.96 (1H, s), 7.37 (1H, s), 7.58 (1H, s), 7.30–7.55 (8H, m), 7.17 (1H, dd), 5.63 (2H, s), 3.74 (3H, s), 3.38 (2H, t, J=8 Hz), 0.74 (2H, t, J=8 Hz), −0.12 (9H, s).

Stage 2: 1 cm³ of 2N HCl is added to a solution of 10.8 mg of 1N-[6-chloro-5-phenyl-1-(2-(trimethylsilanyl)ethoxymethyl)-1H-indazol-3-yl]-3-methoxybenzenesulfonamide in 1 cm³ of methanol. The reaction medium is stirred at ambient temperature for 48 hours and at reflux for 1 hour, then evaporated. The solid obtained is dried under vacuum to give 8 mg of N-(6-chloro-5-phenyl-1H-indazol-3-yl)-3-methoxybenzenesulfonamide (colorless solid).

Mass spectrum: 414[M+H]$^+$; retention time: 4.04 minutes.

$^1$H NMR [d$_6$-DMSO]: 12.90 (1H, broad s), 10.74(1H, broad s), 7.67 (1H, s), 7.31–7.56 (10H, s), 7.20 (1H, dd), 3.77 (3H, s).

The pharmaceutical compositions according to the invention are composed of a compound of formula (I) or a salt of such a compound, in the pure state or in the form of a composition in which it is combined with any other pharmaceutically compatible product, which can be inert or physiologically active. The medicaments according to the invention can be employed orally, parenterally, rectally or topically.

Use may be made, as solid compositions for oral administration, tablets, pills, powders (of hard gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants, such as magnesium stearate or talc, a colorant, a coating (dragées) or a glaze.

Use may be made, as liquid compositions for oral administration, of pharmaceutically acceptable solutions, suspensions, emulsions, syrups and elixirs comprising inert diluents, such as water, ethanol, glycerol, vegetable oils or liquid paraffin. These compositions can comprise substances other than the diluents, for example wetting, sweetening, thickening, flavoring or stabilizing products.

The sterile compositions for parenteral administration can preferably be solutions in aqueous or nonaqueous form, suspensions or emulsions. Use may be made, as solvent or vehicle, of water, propylene glycol, a polyethylene glycol, vegetable oils, in particular olive oil, injectable organic esters, for example ethyl oleate, or other suitable organic solvents. These compositions can also comprise adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in sterile water or any other injectable sterile medium.

The compositions for rectal administration are suppositories or rectal capsules which comprise, in addition to the active product, excipients such as cocoa butter, semisynthetic glycerides or polyethylene glycols.

The compositions for topical administration can be, for example, creams, lotions, eye drops, mouthwashes, nose drops or aerosols.

The subject matter of the invention is the compounds and their use of aminoindazoles of formula (I) and their pharmaceutically acceptable salts in the preparation of pharmaceutical compositions intended to prevent and treat diseases which result from an abnormal activity of kinases, such as, for example, those involved in neurodegenerative diseases, Aizheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer.

Mention may be made, as abnormal kinase activity, of, for example, that of PI3K, AkT or GSK3beta, of CDKs, and the like.

In human therapy, the compounds according to the invention are of particular use in the treatment and/or prevention of neurodegenerative diseases, Alzheimer's disease, Parkinson's disease, frontoparietal dementia, corticobasal degeneration, Pick's disease, strokes, cranial and spinal traumas and peripheral neuropathies, obesity, metabolic diseases, type II diabetes, essential hypertension, atherosclerotic cardiovascular diseases, polycystic ovaries syndrome, syndrome X, immunodeficiency and cancer.

The doses depend on the desired effect, on the duration of the treatment and on the administration route used; they are generally between 5 mg and 1000 mg per day orally for an adult with unit doses ranging from 1 mg to 250 mg of active substance.

Generally, the doctor will determine the appropriate dosage according to the age, weight and all the other factors specific to the subject to be treated.

The following examples illustrate compositions according to the invention:

EXAMPLE A

Hard gelatin capsules, with doses of 50 mg of active product, having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets, with doses of 50 mg of active product, having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol and titanium oxide(72/3.5/24.5) q.s. for 1 coated tablet completed to | 245 mg |

EXAMPLE C

An injectable solution comprising 10 mg of active product having the following composition is prepared:

| | |
|---|---|
| Compound of formula (I) | 10 mg |
| Benzoic acid | 80 mg |

-continued

| | |
|---|---|
| Benzyl alcohol | 0.06 ml |
| Sodium benzoate | 80 mg |
| 95% Ethanol | 0.4 ml |
| Sodium hydroxide | 24 mg |
| Propylene glycol | 1.6 ml |
| Water | q.s. for 4 ml |

The present invention also relates to the method for the prevention and treatment of diseases in which a phosphorylation of the tau protein is involved by administration of a compound of formula (I) and its pharmaceutically acceptable salts.

What is claimed is:
1. A compound of formula (I):

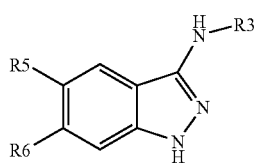

wherein
R3 is a (1–6C)alkyl, aryl, aryl(1–6C)alkyl, heteroaryl, heteroaryl(1–6C)alkyl, aryl or heteroaryl fused to a (1–10C) cycloalkyl, heterocycle, heterocycloalkyl, cycloalkyl, adamantyl, polycycloalkyl, alkenyl, alkynyl, CONR1R2, CSNR1R2, COOR1, SO$_2$R1, C(=NH)R1 or C(=NH)NHR1 radical; these radicals optionally being substituted by 1 or more substituents chosen from halogen, CN, NO$_2$, NH$_2$, OH, OR1, COOH, C(O)OR1, —O—C(O)R1, NR1R2, NHC(O)R1, C(O)NR1R2, SR1, S(O)R1, SO$_2$R1, NHSO$_2$R1, SO$_2$NR1R2, C(S)NR1R2, NHC(S)R1, —O—SO$_2$R1, —SO$_2$—O—R1, aryl, heteroaryl, heterocycle, formyl, trifluoromethyl, trifluoromethylsulfanyl, trifluoromethoxy or (1–6C)alkyl;
R5 is an aryl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl, trifluoromethoxy or (1–6C)alkyl;
R6 is a halogen, methyl, cyclopropyl, CN, OH, methoxy, trifluoromethyl, ethylenyl, acetylenyl, trifluoromethoxy, NO$_2$, NH$_2$ or NMe2 radical;
R1, R2, R10 and R11 are, independently of one another, a hydrogen, (1–6C)alkyl, aryl, alkenyl, alkynyl or heteroaryl, themselves optionally being substituted by 1 or more substituents chosen from halogen, (1–6C)alkyl, (1–6C)alkoxy, CN, NO$_2$, NH$_2$, OH, COOH, COOalkyl, CONH$_2$, formyl, oxo, trifluoromethyl or trifluoromethoxy; or
R1 and R2 can form a 5- or 6-membered ring which may have a heteroatom, such as O, S or N;
or a racemate, enantiomer, diastereoisomer or a mixture thereof, or a tautomer or a pharmaceutically acceptable salt thereof.

2. A compound according to claim 1:
wherein
R1 is a phenyl optionally substituted by 1 or more substituents chosen from halogen, CN, NO$_2$, NH$_2$, OH, OR10, COOH, C(O)OR10, —O—C(O)R10, NR10R11, NHC(O)R10, C(O)NR10R11, NHC(S)R10, C(S)NR10R11, SR10, S(O)R10, SO$_2$R10, NHSO$_2$R10, SO$_2$NR10R11, —O—SO$_2$R10, —SO$_2$—O—R10, aryl, heteroaryl, formyl, trifluoromethyl trifluoromethoxy or (1–6C)alkyl;
or a racemate, enantiomer, diastereoisomer or a mixtures thereof, or a tautomer or a pharmaceutically acceptable salt thereof.

3. A compound selected from the group consisting of:
N-(bicyclo[2.2.1]hept-5-en-2-ylmethyly)-6-chloro-5-phenyl-1H-indazol-3-amine;
6-chloro-N-(3,3dimethylbutyl)-5-phenyl-1H-indazol-3-amine;
6-chloro-N-(3-phenylpropyl)-5-phenyl-1H-indazol-3-amine;
6-chloro-N-(cyclopropylmethyl)-5-phenyl-1H-indazol-3-amine;
6-chloro-N-(cyclopentylmethyl)-5-phenyl-1H-indazol-3-amine;
6-chloro-N-[3-(methylthio)propyl]-5-phenyl-1H-indazol-3-amine;
6-chloro-N-(phenylethyl)-5-phenyl-1H-indazol-3-amine;
6-chloro-N-(cyclohexylmethyl)-5-phenyl-1H-indazol-3-amine;
6-chloro-N-propyl-5-phenyl-1H-indazol-3-amine;
6-chloro-N-(2,2,3,3,4,4,4-heptafluorobutyl)-5-phenyl-1H-indazol-3-amine hydrate;
6-chloro-N-(4,4,4-trifluorobutyl)-5-phenyl-1H-indazol-3-amine;
6-chloro-N-[(4-methoxyphenyl)methyl]-5-phenyl-1H-indazol-3-amine;
6-chloro-N-(phenylmethyl)-5-phenyl-1H-indazol-3-amine;
6-chloro-N-[(4-cyanophenyl)methyl]-5-phenyl-1H-indazol-3-amine;
N-[(4-chlorophenyl)methyl]-6-chloro-5-phenyl-1H-indazol-3-amine;
6-chloro-N-[(3-methoxyphenyl)methyl]-5-phenyl-1H-indazol-3-amine;
6-chloro-N-[[4-(trifluoromethoxy)phenyl]methyl]-5-phenyl-1H-indazol-3-amine;
N-[4-[[[6-chloro-5-phenyl-1H-indazol-3-yl]amino]methyl]phenyl]acetamide;
6-chloro-N-[(3,5dichlorophenyl)methyl]-5-phenyl-1H-indazol-3-amine;
6-chloro-5-phenyl-N-[[4-(trifluoromethyl)phenyl]methyl]-1H-indazol-3-amine;
6-chloro-N-[(4-fluorophenyl)methyl]-5-phenyl-1H-indazol-3-amine;
6-chloro-N-[3-(4-methylphenoxy)phenylmethyl]-5-phenyl-1H-indazol-3-amine;
N-(2,2,3,3,4,4,4heptafluorobutyl)-6-chloro-5-phenyl-1H-indazol-3-amine;
6-chloro-5-phenyl-N-[[3,5-bis(trifluoromethyl)phenyl]methyl]-1H-indazol-3-amine;
6-chloro-5-phenyl-N-[[3-(trifluoromethyl)phenyl]methyl]-1H-indazol-3-amine;
6-chloro-N-[(6methoxy-2-naphthyl)methyl]-5-phenyl-1H-indazol-3-amine;
6-chloro-N-[(pentafluorophenyl)methyl]-5-phenyl-1H-indazol-3-amine;

6-chloro-N-[[4-(methylthio)phenyl]methyl]-5-phenyl-1H-indazol-3-amine;
N-[(4-chloro-3-fluorophenyl)methyl]-6-chloro-5-phenyl-1H-indazol-3-amine;
6-chloro-5-phenyl-N-(3,3,3-trifluoropropyl)-1H-indazol-3-amine;
6-chloro-5-phenyl-N-(3-thienylmethyl)-1H-indazol-3-amine;
N-(bicyclo[2.2.1]hept-5-en-2-ylmethyl)-6-chloro-5-phenyl-1H-indazol-3-amine;
N-(1,1'-biphenyl-4-ylmethyl)-6-chloro-5-phenyl-1H-indazol-3-amine;
6-chloro-N-[[4-(dimethylamino)phenyl]methyl]-5-phenyl-1H-indazol-3-amine;
N-(2,2'-bithiophen-5-ylmethyl)-6-chloro-5-phenyl-1H-indazol-3-amine;
6-chloro-5-phenyl-N-[[1-(phenylmethyl)-1-H-imidazol-2-yl]methyl]-1H-indazol-3-amine;
6-chloro-N-[[1-methyl-1H-imidazol-2-yl]-methyl]-5-phenyl-1H-indazol-3-amine;
6-chloro-N-[(1-methyl-1H-indazol-3-yl)methyl]-5-phenyl-1H-indazol-3-amine;
6-chloro-N-[(5-methyl-2-furanyl)methyl]-5-phenyl-1H-indazol-3-amine;
6-chloro-5-phenyl-N-(1H-pyrrol-2-ylmethyl)-1H-indazol-3-amine;
6-chloro-5-phenyl-N-[(1H-imidazol-2-yl)methyl]-1H-indazol-3-amine;
6-chloro-5-phenyl-N-[(1H-imidazol-4-yl)methyl]-1H-indazol-3-amine;
6-chloro-5-phenyl-N-[(1H-pyrazol-3-ylmethyl)-1H-indazol-3-amine;
6-chloro-N-[[2methyl-1H-imidazol-4-yl]methyl]-5-phenyl-1H-indazol-3-amine;
6-chloro-N-[(3,5-dimethyl-1-phenyl-1H-pyrazol-4-yl)methyl]-5-phenyl-1H-indazol-3-amine;
6-chloro-5-phenyl-N-[[2-phenyl-1H-imidazol-4-yl]methyl]1H-indazol-3-amine;
6-chloro-N-[[5-(4chlorophenyl)-2-furanyl]methyl]-5-phenyl-1H-indazol-3-amine;
6-chloro-5-phenyl-N-[(1-methyl-1H-pyrrol-2-yl)methyl]-1H-indazol-3-amine;
4-[5-[[[6-chloro-5-phenyl-1H-indazol-3-yl]-amino]methyl]-2-furanyl]-benzenesulfonamide;
6-chloro-5-phenyl-N-(3-thienylmethyl)-1H-indazol-3-amine;
6-chloro-5-phenyl-N-[[2-phenyl-1H-imidazol-4-yl]methyl]-1H-indazol-3-amine;
ethyl2-[[[6-chloro-5-phenyl-1H-indazol-3-yl]amino]methyl]-5-(methylthio)-1H-imidazol-4-carboxylate;
6-chloro-5-phenyl-N-[[5-[4-(trifluoromethyl)phenyl]-2-furanyl]methyl]-1H-indazol-3-amine;
6-chloro-5-phenyl-N-[2-(1-piperidinyl)ethyl]-1H-indazol-3-amine;
6-chloro-N-[2-(4-morpholinyl)ethyl]-5-phenyl-1H-indazol-3-amine;
N-(6-chloro-5-phenyl-1H-indazol-3-yl)-N'-(3,5-dichlorophenyl)urea;
N-(6-chloro-5-phenyl-1H-indazol-3-yl)-N'-(2-propenyl)urea;
N-(5-chloro-5-phenyl-1H-indazol-3-yl)-N'-(phenylmethyl)urea;
N-(6-chloro-5-phenyl-1H-indazol-3-yl)-N'-(4-phenoxyphenyl)urea;
N-(6-chloro-5-phenyl-1H-indazol-3-yl)-N'-(4-methoxyphenyl)methyl]urea;
N-(6-chloro-5-phenyl-1H-indazol-3-yl)-N'-[4-(trifluoromethyl)phenyl]urea;
N-(6-chloro-5-phenyl-1H-indazol-3-yl)-N'-(4-methoxyphenyl)urea;
N-(6-chloro-5-phenyl-1H-indazol-3-yl)-N'-cyclohexylurea;
N-(6-chloro-5-phenyl-1H-indazol-3-yl)-N'-propylurea;
N-(6-chloro-5-phenyl-1H-indazol-3-yl)-N'-(4-chlorophenyl)urea;
N-(6-chloro-5-phenyl-1H-indazol-3-yl)-N'-(4-fluorophenyl)urea;
N-[6-chloro-5-phenyl-1H-indazol-3-yl]-N'-(tricyclo[3.3.1.1$^{3,7}$]dec)-1-ylurea;
N-(6-chloro-5-phenyl-1H-indazol-3-yl)-N'-(4methylphenyl)urea;
N-[6-chloro-5-phenyl-1H-indazol-3-yl]-4-methyl-benzenesulfonamide;
N-[6-chloro-5-phenyl-1H-indazol-3-yl]methanesulfonamide;
N-[6-chloro-5-phenyl-1H-indazol-3-yl]-2-propanesulfonamide;
N-[6-chloro-5-phenyl-1H-indazol-3-yl]-2,2,2-trifluoroethanesulfonamide;
N-[6-chloro-5-phenyl-1H-indazol-3-yl]-2-thiophenesulfonamide;
N-[6-chloro-5-phenyl-1H-indazol-3-yl]benzenesulfonamide;
N-[6-chloro-5-phenyl-1H-indazol-3-yl]-4-(trifluoromethyl)benzenesulfonamide;
N-[6-chloro-5-phenyl-1H-indazol-3-yl]-5-(3-isoxazolyl)-2-thiophenesulfonamide;
N-[6-chloro-5-phenyl-1H-indazol-3-yl]-4-fluorobenzenesulfonamide;
N-[6-chloro-5-phenyl-1H-indazol-3-yl]-4-methoxybenzenesulfonamide;
N-[6-chloro-5-phenyl-1H-indazol-3-yl]benzenemethanesulfonamide;
N-[6-chloro-5-phenyl-1H-indazol-3-yl]-1-methyl-1H-imidazole4-sulfonamide;
N-[6-chloro-5-phenyl-1H-indazol-3-yl]-4-(1,1-dimethylethyl)benzenesulfonamide;
N-[4-[[(6-chloro-5-phenyl-1H-indazol-3-yl)amino]sulfonyl]phenyl]acetamide;
N-[6-chloro-5-phenyl-1H-indazol-3-yl]-4-methylbenzenemethanesulfonamide;
6-chloro-N-(pentafluorophenyl)-5-phenyl-1H-indazol-3-amine;
6-chloro-N-(3,4-difluorophenyl)-5-phenyl-1H-indazol-3-amine;
6-chloro-5-phenyl-N-(2,3,5,6-tetrafluorophenyl)-1H-indazol-3-amine;
6-chloro-5-phenyl-N-(2,4,6-trifluorophenyl)-1H-indazol-3-amine;
6-chloro-N-(4-fluorophenyl)-5-phenyl-1H-indazol-3-amine;
6-chloro-N-[3-(trifluoromethyl)phenyl]-5-phenyl-1H-indazol-3-amine;
6-chloro-N-[4-(trifluoromethyl)phenyl]-5-phenyl-1H-indazol-3-amine;
6-chloro-N-[3-fluoro-5-(trifluoromethyl)phenyl]-5-phenyl-1H-indazol-3-amine;
6-chloro-N-(4-nitrophenyl)-5-phenyl-1H-indazol-3-amine;
6-chloro-N-(3-nitrophenyl)-5-phenyl-1H-indazol-3-amine;
6-chloro-N-(3-methoxyphenyl)-5-phenyl-1H-indazol-3-amine;

6-chloro-N-(4-methoxyphenyl)-5-phenyl-1H-indazol-3-amine;
6-chloro-N,5-diphenyl-1H-indazol-3-amine;
6-chloro-N-(1-pyridinyl)-5-phenyl-1H-indazol-3-amine; and
6-chloro-N-(2-pyridinyl)-5-phenyl-1H-indazol-3-amine;
or a racemate, enantiomer, diastereoisomer or a mixture thereof, or a tautomer or a pharmaceutically acceptable salt thereof.

4. A compound selected from the group consisting of:
N-butyl-6-Chloro-5-phenyl-1H-indazol-3-amine
3-(6-Chloro-5-phenyl-1H-indazol-3-ylamino)thiophene-2-carbonitrile;
(6-Chloro-5-phenyl-1H-indazol-3-yl)(pyridin-2-yl)amine;
(6-Chloro-5-phenyl-1H-indazol-3-yl)(5-nitropyridin-2-yl)amine;
(6-Chloro-5-phenyl-1H-indazol-3-yl)(6-methoxypyridin-2-yl)amine;
N-(6-Chloro-5-phenyl-1H-indazol-3-yl)-N'-phenylurea;
1-(6-Chloro-5-phenyl-1H-indazol-3-yl)-3-(4-ethoxyphenyl)urea;
1-(6-Chloro-5-phenyl-1H-indazol-3-yl)-3-(3,4-dichlorophenyl)urea;
3[-(3-(6-Chloro-5-phenyl-1H-indazol-3-yl)ureido]propionic acid methyl ester;
1-(6-Chloro-5-phenyl-1H-indazol-3-yl)-3-(4-dimethylamino)phenyl)urea;
1-(6-Chloro-5-phenyl-1H-indazol-3-yl)-3-isopropylurea;
1-(6-Chloro-5-phenyl-1H-indazol-3-yl)-3-cyclohexylurea;
1-(6-Chloro-5-phenyl-1H-indazol-3-yl)-3-(3-(trifluoromethyl)phenyl)urea;
1-(6-Chloro-5-phenyl-1H-indazol-3-yl)-3-(2-(thiophen-2-yl)ethyl)urea;
1-(1,3-Benzodioxol-5-yl)-3-(6-Chloro-5-phenyl-1H-indazol-3-yl)urea;
1-(6-Chloro-5-phenyl-1H-indazol-3-yl)-3-(3,5-dimethylisoxazol-4-yl)urea;
1-Benzyl-3-(6-Chloro-5-phenyl-1H-indazol-3-yl)urea;
1-(6-Chloro-5-phenyl-1H-indazol-3-yl)-3-(phenethyl)thiourea;
1-(6-Chloro-5-phenyl-1H-indazol-3-yl)-3-[3-(4-methylpiperazin-1-yl)propyl]urea;
1-(6-Chloro-5-phenyl-1H-indazol-3-yl)-3-(3-imidazol-1-yl)propyl)urea;
1-(6-Chloro-5-phenyl-1H-indazol-3-yl)-3-(2-hydroxyethyl)urea;
1-(6-Chloro-5-phenyl-1H-indazol-3-yl)-3-[3-(4-methylpiperazin-1-yl)propyl]urea;
Pyrrolidine-1-carboxylic acid (6-chloro-5-phenyl-1H-indazol-3-yl)amide;
(6-Chloro-5-phenyl-1H-indazol-3-yl)carbamic acid methyl ester;
(6-Chloro-5-phenyl-1H-indazol-3-yl)urea;
(6-Chloro-5-phenyl-1H-indazol-3-yl)carbamic acid benzyl ester;
(6-Chloro-5-phenyl-1H-indazol-3-yl)carbamic acid allyl ester;
(6-Chloro-5-phenyl-1H-indazol-3-yl)carbamic acid isobutyl ester;
Piperidine-1-carboxylic acid (6-chloro-5-phenyl-1H-indazol-3-yl)amide;
1-(3-(Azetidin-1-yl)propyl)-3-((6-chloro-5-phenyl-1H-indazol-3-yl)urea;
1-(6-Chloro-5-phenyl-1H-indazol-3-yl)-3-(3-chloropropyl)urea;
1-(6,7-Difluoro-5-phenyl-1H-indazol-3-yl)-3-(3-imidazol-1-yl)propyl)urea;
1-(3-(Aminopropyl)-3-(6-chloro-5-phenyl-1H-indazol-3-yl)urea;
1-(6-Chloro-5-phenyl-1H-indazol-3-yl)-3-[4-(4-pyridin-3-yl)imidazol-1-yl)-butyl]urea;
1-(6-Chloro-5-phenyl-1H-indazol-3-yl)-3-(2-pyrrolidin-1-yl)-ethyl)urea;
2,5-Dimethylpyrrolidine-1-carboxylic acid (6-chloro-5-phenyl-1H-indazol-3-yl)amide;
N-(6-Chloro-5-phenyl-1H-indazol-3-yl)acetamidine;
N-(6-Chloro-5-phenyl-1H-indazol-3-yl)-6-methoxypyrazine-2-carboximidine;
N-(6-Chloro-5-phenyl-1H-indazol-3-yl)benzamidine;
N-(6-Chloro-5-phenyl-1H-indazol-3-yl)-pyridine-2-carboximidine; and
N-(6-chloro-5-phenyl-1H-indazol-3-yl)-3-methoxybenzenesulfonamide;
or a racemate, enantiomer or a tautomer or a pharmaceutically acceptable salt thereof.

5. A pharmaceutical composition, comprising, in a pharmaceutically acceptable medium, a compound according to claim 1.

6. A pharmaceutical composition, comprising, in a pharmaceutically acceptable medium, a compound according to claim 2.

* * * * *